(12) United States Patent
Berg et al.

(10) Patent No.: US 10,398,376 B2
(45) Date of Patent: Sep. 3, 2019

(54) GARMENT INTEGRATED ELECTRICAL INTERFACE SYSTEM AND METHOD OF MANUFACTURE

(71) Applicant: Mad Apparel, Inc., Redwood City, CA (US)

(72) Inventors: James Artel Berg, Redwood City, CA (US); Gaston MacMillan, Redwood City, CA (US); Chris Glaister, Redwood City, CA (US); Wesley Groom, Redwood City, CA (US); Liang Yao, Redwood City, CA (US)

(73) Assignee: Mad Apparel, Inc., Redwood City, CA (US)

( * ) Notice: Subject to any disclaimer, the term of this patent is extended or adjusted under 35 U.S.C. 154(b) by 1009 days.

(21) Appl. No.: 14/869,398

(22) Filed: Sep. 29, 2015

(65) Prior Publication Data
US 2016/0270727 A1 Sep. 22, 2016

Related U.S. Application Data

(63) Continuation-in-part of application No. 14/742,420, filed on Jun. 17, 2015.
(Continued)

(51) Int. Cl.
*A61B 5/00* (2006.01)
*H05K 1/11* (2006.01)
(Continued)

(52) U.S. Cl.
CPC .......... *A61B 5/6804* (2013.01); *A61B 5/0006* (2013.01); *A61B 5/02055* (2013.01);
(Continued)

(58) Field of Classification Search
CPC . A61B 5/0402; A61B 5/0408; A61B 5/04085; A61B 5/0422; A61B 5/04284;
(Continued)

(56) References Cited

U.S. PATENT DOCUMENTS 3,498,291 A * 3/1970 Bunn ................... A61B 5/0408
600/372
3,534,727 A 10/1970 Roman
(Continued)

FOREIGN PATENT DOCUMENTS

| KR | 10-2014-0008971 A | 1/2014 |
| WO | WO 01/15286 A1 | 3/2001 |
| WO | 2006119345 A2 | 11/2006 |
| WO | WO 2007/063436 A1 | 6/2007 |

OTHER PUBLICATIONS

StudSeal Press Release, Douglas Electrical Components, May 21, 2009, 4 pages, May be Retrieved at<URL:http://news.thomasnet.com/fullstory/hermetic-feedthroughs-suit-high-current-applications-827050>.
(Continued)

*Primary Examiner* — Eun Hwa Kim
(74) *Attorney, Agent, or Firm* — Fenwick & West LLP

(57) ABSTRACT

A system for electrically coupling a garment to a mating object and manufacture method thereof, the system comprising: a fabric interlayer of the garment including a set of ports; an electronics substrate having a first surface adjacent to a second side of the fabric interlayer and including a set of vias through a thickness of the electronics substrate, aligned with the set of ports, and a set of contacts at a second surface opposing the first surface; a mount assembly having a third surface adjacent to the second surface of the electronics substrate and including a set of holes aligned with the set of vias and the set of ports, as well as a set of openings that correspond to and receive portions of the set of contacts,
(Continued)

and a fourth surface opposing the third surface and defining a cavity configured to receive and electrically interface the mating object to the electronics substrate; and a set of fasteners that 1) compress the backing plate, the fabric interlayer, the electronics substrate, and the mount assembly by way of the set of ports, the set of vias, and the set of holes in supporting a waterproof seal, and 2) electrically couple the set of embedded ports to the set of vias.

19 Claims, 15 Drawing Sheets

Related U.S. Application Data

(60) Provisional application No. 62/013,405, filed on Jun. 17, 2014, provisional application No. 62/016,373, filed on Jun. 24, 2014, provisional application No. 62/057,226, filed on Sep. 29, 2014, provisional application No. 62/153,904, filed on Apr. 28, 2015.

(51) Int. Cl.
| | |
|---|---|
| *A61B 5/0402* | (2006.01) |
| *A61B 5/0476* | (2006.01) |
| *A61B 5/0488* | (2006.01) |
| *A61B 5/0205* | (2006.01) |
| *H01R 12/77* | (2011.01) |
| *A61B 5/04* | (2006.01) |
| *A61B 5/11* | (2006.01) |

(52) U.S. Cl.
CPC .............. *A61B 5/04* (2013.01); *A61B 5/0402* (2013.01); *A61B 5/0476* (2013.01); *A61B 5/0488* (2013.01); *A61B 5/1118* (2013.01); *A61B 5/7203* (2013.01); *H01R 12/774* (2013.01); *H05K 1/116* (2013.01); *A61B 5/0024* (2013.01); *A61B 2562/125* (2013.01); *D05D 2303/40* (2013.01); *H01R 2201/20* (2013.01)

(58) Field of Classification Search
CPC .............. A61B 5/0432; A61B 5/04325; A61B 256/226; A61B 256/227; A61B 5/6804; A61B 5/6805; A61B 5/6806; A61B 5/6807; A61B 5/6808; H01R 12/774; H01R 2201/20; D05D 2303/40; H05K 1/116
See application file for complete search history.

(56) References Cited

U.S. PATENT DOCUMENTS

| | | | |
|---|---|---|---|
| 3,973,099 | A | 8/1976 | Morris |
| 3,982,529 | A | 9/1976 | Sato |
| 4,400,341 | A | 8/1983 | Sorensen |
| 4,706,680 | A | 11/1987 | Keusch et al. |
| 4,729,377 | A | 3/1988 | Granek et al. |
| 4,799,441 | A | 1/1989 | Boser |
| 6,002,957 | A | 12/1999 | Finneran |
| 6,319,015 | B1 * | 11/2001 | Faunce ................ H01R 11/22 24/662 |
| 6,350,129 | B1 | 2/2002 | Gorlick |
| 6,381,482 | B1 | 4/2002 | Jayaraman et al. |
| 6,970,731 | B1 | 11/2005 | Jayaraman et al. |
| 6,978,684 | B2 | 12/2005 | Nurse |
| 7,173,437 | B2 | 2/2007 | Hervieux et al. |
| 7,474,910 | B2 | 1/2009 | Hassonjee et al. |
| 7,559,902 | B2 | 7/2009 | Ting et al. |
| 7,602,301 | B1 | 10/2009 | Stirling et al. |
| 7,783,334 | B2 | 8/2010 | Nam et al. |
| 7,821,407 | B2 | 10/2010 | Shears et al. |
| 7,825,815 | B2 | 11/2010 | Shears et al. |
| 7,978,081 | B2 | 7/2011 | Shears et al. |
| 8,006,633 | B2 | 8/2011 | Bennett et al. |
| 8,032,199 | B2 | 10/2011 | Linti et al. |
| 8,146,171 | B2 | 4/2012 | Chung et al. |
| 8,214,007 | B2 | 7/2012 | Baker et al. |
| 8,267,701 | B2 | 9/2012 | Beaman et al. |
| 8,280,503 | B2 | 10/2012 | Linderman |
| 8,475,371 | B2 | 7/2013 | Derchak et al. |
| 8,560,044 | B2 | 10/2013 | Kurzweil et al. |
| 8,750,959 | B2 | 6/2014 | Lindberg et al. |
| 8,798,708 | B2 | 8/2014 | Tremblay |
| 8,818,478 | B2 | 8/2014 | Scheffler et al. |
| 8,821,305 | B2 | 9/2014 | Cusey et al. |
| 8,909,318 | B2 | 12/2014 | Nordstrom |
| 2004/0187184 | A1 | 9/2004 | Rubin et al. |
| 2004/0254624 | A1 | 12/2004 | Johnson |
| 2005/0177059 | A1 | 8/2005 | Koivumaa et al. |
| 2005/0178201 | A1 | 8/2005 | Impio et al. |
| 2006/0264730 | A1 | 11/2006 | Stivoric et al. |
| 2007/0038057 | A1 | 2/2007 | Nam et al. |
| 2007/0285868 | A1 | 12/2007 | Lindberg et al. |
| 2008/0092341 | A1 | 4/2008 | Ahmadshahi |
| 2008/0096726 | A1 | 4/2008 | Riley et al. |
| 2008/0278899 | A1 | 11/2008 | Hotelling et al. |
| 2008/0288026 | A1 | 11/2008 | Cross et al. |
| 2009/0012408 | A1 | 1/2009 | Nagata et al. |
| 2009/0024017 | A1 | 1/2009 | Ruffini et al. |
| 2009/0054758 | A1 * | 2/2009 | Dunseath ................ A61B 5/05 600/421 |
| 2009/0270689 | A1 | 10/2009 | Galland |
| 2010/0037489 | A1 | 2/2010 | Berner et al. |
| 2010/0041974 | A1 | 2/2010 | Ting et al. |
| 2010/0117837 | A1 | 5/2010 | Stirling et al. |
| 2010/0185398 | A1 | 7/2010 | Berns et al. |
| 2010/0204616 | A1 | 8/2010 | Shears et al. |
| 2010/0234715 | A1 | 9/2010 | Shin et al. |
| 2010/0251454 | A1 | 10/2010 | Kiernan |
| 2010/0324405 | A1 | 12/2010 | Niemi et al. |
| 2011/0015498 | A1 | 1/2011 | Mestrovic et al. |
| 2011/0257546 | A1 | 10/2011 | Gozzini et al. |
| 2011/0288605 | A1 | 11/2011 | Kaib et al. |
| 2012/0068759 | A1 | 3/2012 | Clark et al. |
| 2012/0165645 | A1 | 6/2012 | Russell et al. |
| 2012/0208156 | A1 | 8/2012 | Rocklin |
| 2012/0330126 | A1 | 12/2012 | Hoppe et al. |
| 2013/0077263 | A1 | 3/2013 | Oleson et al. |
| 2013/0137943 | A1 | 5/2013 | Rodrigues |
| 2013/0137956 | A1 | 5/2013 | Okuda et al. |
| 2013/0172722 | A1 | 7/2013 | Ninane et al. |
| 2013/0192071 | A1 | 8/2013 | Esposito et al. |
| 2013/0198867 | A1 | 8/2013 | Ricci et al. |
| 2013/0245388 | A1 | 9/2013 | Rafferty et al. |
| 2013/0261422 | A1 | 10/2013 | Gilmore et al. |
| 2013/0324368 | A1 | 12/2013 | Aragones et al. |
| 2014/0070949 | A1 | 3/2014 | Chen |
| 2014/0070957 | A1 | 3/2014 | Longinotti-Buitoni et al. |
| 2014/0097944 | A1 | 4/2014 | Fastert et al. |
| 2014/0135887 | A1 * | 5/2014 | Totman ................ A61N 1/046 607/142 |
| 2014/0172134 | A1 | 6/2014 | Meschter |
| 2014/0180023 | A1 | 6/2014 | Stivoric et al. |
| 2014/0189928 | A1 | 7/2014 | Oleson et al. |
| 2014/0275888 | A1 | 9/2014 | Wegerich et al. |
| 2014/0296651 | A1 | 10/2014 | Stone |
| 2014/0307423 | A1 | 10/2014 | Coats |
| 2014/0343391 | A1 | 11/2014 | Korkala et al. |
| 2014/0352023 | A1 | 12/2014 | Mordecai et al. |
| 2015/0047091 | A1 | 2/2015 | Fournier et al. |
| 2015/0148619 | A1 | 5/2015 | Berg et al. |
| 2015/0181692 | A1 | 6/2015 | Jezewski et al. |

OTHER PUBLICATIONS

European Extended Search Report, European Application No. 15847342. 1, dated Mar. 13, 2018, 8 pages.

(56) References Cited

OTHER PUBLICATIONS

European Extended Search Report, European Application No. 15809222.1, dated Mar. 29, 2018, 9 pages.
United States Office Action, U.S. Appl. No. 14/541,446, dated Jun. 27, 2018, 28 pages.
PCT International Search Report, PCT Application No. PCT/US15/52969, dated Dec. 29, 2015, 11 pages.
United States Office Action, U.S. Appl. No. 14/742,420, dated Aug. 27, 2018, 17 pages.

* cited by examiner

GARMENT INTEGRATED ELECTRICAL INTERFACE SYSTEM AND METHOD OF MANUFACTURE

CROSS-REFERENCE TO RELATED APPLICATIONS

This application is a continuation-in-part application of U.S. application Ser. No. 14/742,420 filed 17 Jun. 2015, which claims the benefit of U.S. Provisional Application Ser. No. 62/013,405 filed 17 Jun. 2014, and U.S. Provisional Application Ser. No. 62/016,373 filed 24 Jun. 2014, which are each incorporated in its entirety herein by this reference.

This application also claims the benefit of U.S. Provisional Application Ser. No. 62/057,226 filed 29 Sep. 2014, and U.S. Provisional application Ser. No. 62/153,904 filed 28 Apr. 2015, which are each incorporated in its entirety herein by this reference.

TECHNICAL FIELD

This invention relates generally to the biometric device field, and more specifically to a new and useful garment integrated electrical interface system and method of manufacture.

BACKGROUND

Tracking biometric parameters resulting from periods of physical activity can provide profound insights into improving one's performance and overall health. Historically, users have tracked their exercise behavior by manually maintaining records of aspects of their physical activity, including time points, durations, and/or other metrics (e.g., weight lifted, distance traveled, repetitions, sets, etc.) of their exercise behavior. Exercise tracking systems and software have been recently developed to provide some amount of assistance to a user interested in tracking his/her exercise behavior; however, such systems and methods still suffer from a number of drawbacks. In particular, many systems require a significant amount of effort from the user (e.g., systems rely upon user input prior to and/or after a period of physical activity), capture insufficient data (e.g., pedometers that estimate distance traveled, but provide little insight into an amount of physical exertion of the user), provide irrelevant information to a user, and are incapable of detecting body-responses to physical activity at a resolution sufficient to provide the user with a high degree of body awareness. Other limitations of conventional biometric monitoring devices include one or more of: involvement of single-use electrodes, involvement of electrodes that have limited reusability, involvement of a single electrode targeting a single body location, involvement of a professional for electrode placement, use of adhesives for electrode placement, electrode configurations that result in user discomfort (e.g., strap-based systems), use of electrode configurations that are unsuited to motion-intensive activities of the user, use of wired systems that constrain mobility, and other deficiencies.

Furthermore, integration of biometric tracking systems into garments worn by a user is particularly challenging. Challenges include: coupling conductors to garments in a manner that still allows the garment to move and stretch with motion of the user; preventing a conducting fluid (e.g., sweat) from shorting various conductors coupled to a garment; creating an assembly that can be washed and reused without compromising the circuitry and processors through which the system operates; routing signal conduction pathways across seams of a garment; accommodating a high connection density; customizing garment fit to a user; transmitting signals acquired by way of the garment to a processing system; and designing for aesthetics, scalability, and maintaining electrode-skin contact during use by a user.

There is thus a need in the biometric device field to create a new and useful garment integrated electrical interface system and method of manufacture. This invention provides such a new and useful system and method of manufacture.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1:
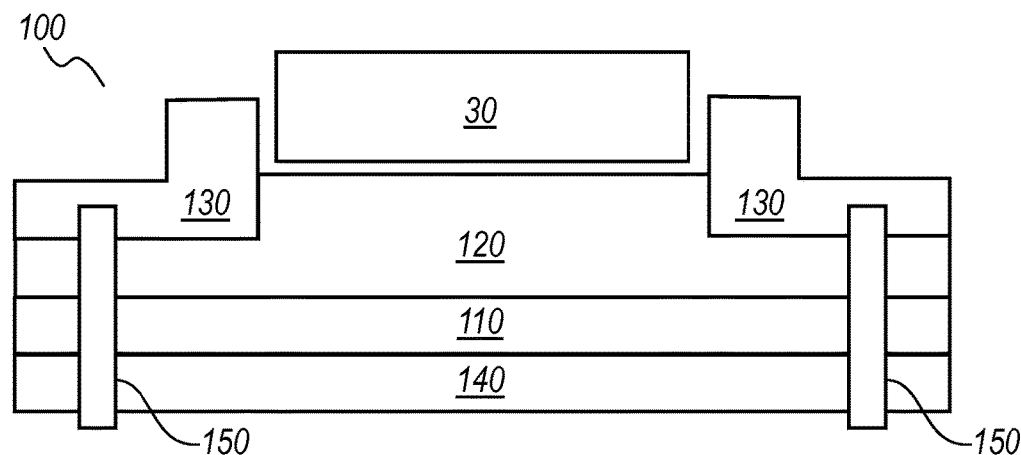
FIG. 1 depicts a cross sectional view of an example embodiment of a system 100 for conducting electrical signals from a garment to a data acquisition device.
Figure 2:
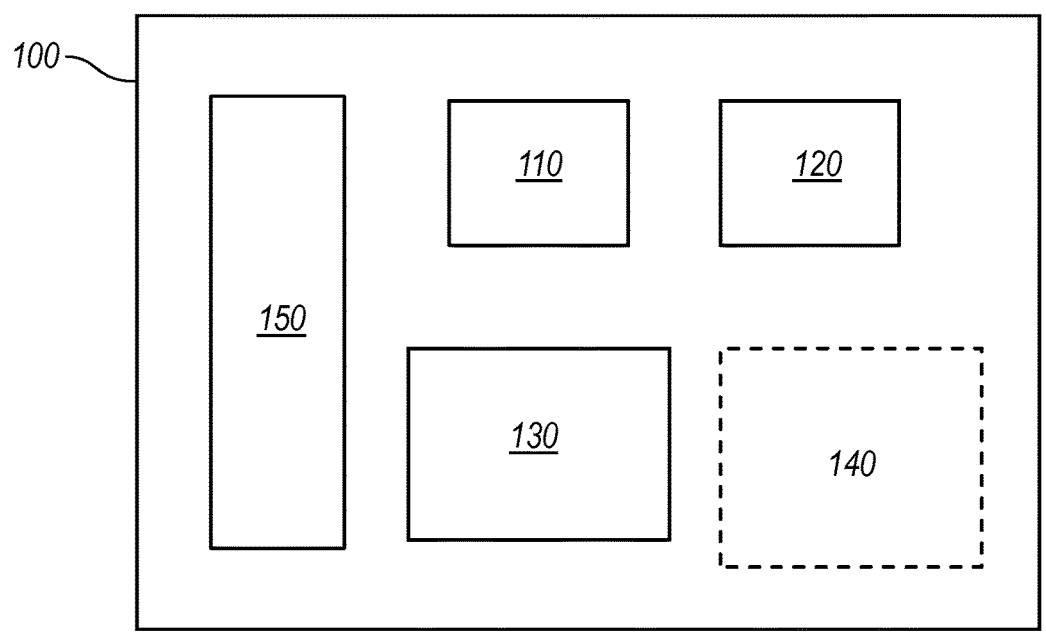
FIG. 2 depicts a schematic of an example embodiment of the system 100.
Figure 3:
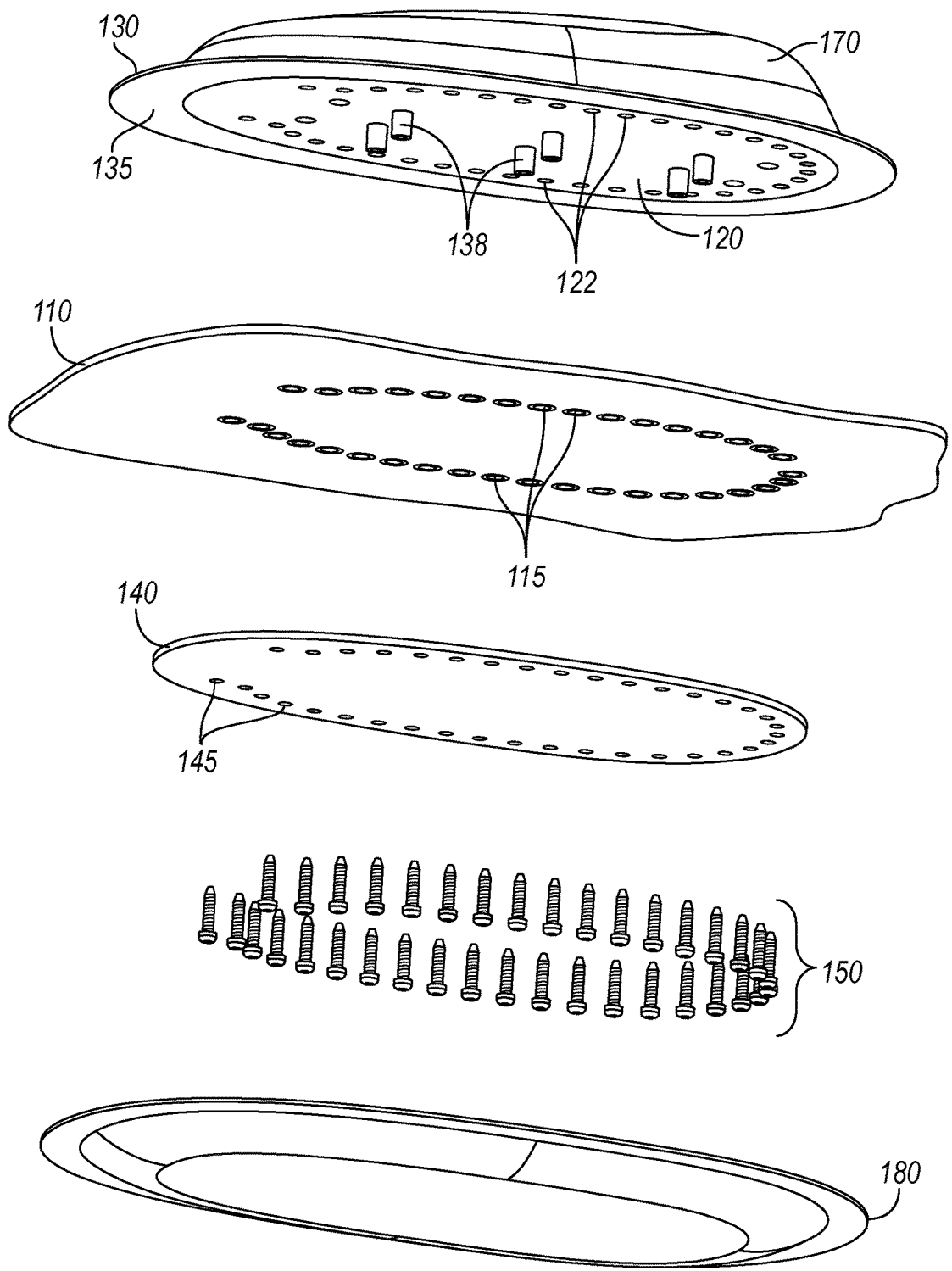
FIG. 3 depicts a first exploded view of an example embodiment of the system 100.

As shown in FIGS. 1-3, an embodiment of a system 100 for electrically coupling a garment to a mating object 30 includes: a fabric interlayer 110 of the garment including a set of ports 115; a backing plate 140, adjacent to a first side of the fabric interlayer 110, including a set of through holes aligned with the set of ports 115; an electronics substrate 120 having a first surface adjacent to a second side of the fabric interlayer no and including a set of vias 122 through a thickness of the electronics substrate 120, aligned with the set of through holes and the set of ports 115, and a set of contacts at a second surface opposing the first surface; a mount assembly 130 having a third surface adjacent to the second surface of the electronics substrate 120 and including a set of holes aligned with the set of vias 122, the set of ports 115, and the set of through holes, as well as a set of openings 132 that correspond to and receive portions of the set of contacts, and a fourth surface opposing the third surface and defining a cavity 131 configured to receive and electrically interface the mating object 30 to the electronics substrate 120; and a set of fasteners 150 that 1) compress the backing plate 140, the fabric interlayer 110, the electronics substrate 120, and the mount assembly 130 by way of the set of through holes, the set of ports 115, the set of vias 122, and the set of holes in supporting a waterproof seal 134, and 2) electrically couple the set of ports 115 to the set of vias 122. As described in more detail below, one or more variations of the system 100 can omit one or more of the above elements, in providing a suitable interface between a garment and a mating object.

The system 100 functions to facilitate transmission of biometric signals from the fabric interlayer 110 to the mating object 30 (e.g., a portable control module as described herein), wherein the biometric signals can be detected from a user who is performing some type of physical activity and subsequently processed to provide information to the user in substantially near real time, such that the user can gain insights into how to maintain or improve performance of the physical activity in a beneficial manner. The system 100 can additionally or alternatively function to protect signal conductor connections, insulate and isolate signal conductors in communication with the system 100, shield the signal conductor connections from noise sources, alter the arrangement of signal conductor contact points between the fabric interlayer no and the mating object 30, and provide a secure retention location for the mating object 30. As such, the system 100 can be used to transfer biometric signals (or other signals) in a manner that has improved wash durability, improved comfort and fit, improved appearance compared to conventional options, and improved integration between the mating object(s) 30 and the garment.

In variations, the system 100 is configured to facilitate transmission of detected bioelectrical signals generated at multiple body regions of a user who is exercising (e.g., performing aerobic exercise, performing anaerobic exercise), wherein a plurality of electrode units in communication with the system 100 can be positioned at multiple body regions of the user, in order to generate a holistic representation of one or more biometric parameters relevant to activity of the user. As such, bioelectrical signals transmittable by the system 100 can include any one or more of: electromyography (EMG) signals, electrocardiography (ECG) signals, electroencephalograph (EEG) signals, galvanic skin response (GSR), bioelectrical impedance (BIA), and any other suitable bioelectrical signal of the user. The system 100 can, however, be configured to transmit any other suitable biosignal data of the user, including one or more of: muscle activity data, heart rate data, movement data, respiration data, location data, skin temperature data, environmental data (e.g., temperature data, light data, etc.), and any other suitable data. Additionally or alternatively, the system 100 can be configured to transmit any other suitable type of electrical signal, including one or more of: audio signals, communication signals, human produced signals, device produced signals, and any other type of signal that can be transferred through a conductive medium.

Preferably, the system 100 is configured to be integrated with a garment 400 worn by a user during a period of physical activity, as described in U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, U.S. application Ser. No. 14/079,621, entitled "Wearable Performance Monitoring, Analysis, and Feedback Systems and Methods" and filed on 30 Jan. 2014, U.S. application Ser. No. 14/699,730, entitled "Biometric Electrode System and Method of Manufacture" and filed on 29 Apr. 2015, and U.S. application Ser. No. 14/724,420, entitled "Biometric Signal Conduction System and Method of Manufacture" and filed on 17 Jun. 2015, each of which is incorporated herein in its entirety by this reference. As such, the system 100 is preferably configured to provide a liquid-tight interface (e.g., by way of a seal) between conductive components of the garment and conductive receptors on the mating object 30, upon coupling of the mating object 30 to the system 100, such that sweat or water which may be intermingled with the fabric(s) of the garment cannot penetrate the system 100 and interfere with sensitive portions (e.g., conductive leads) of the system 100 during use. Even further, in relation to integration with a garment 400, the system 100 is preferably configured to be washable (i.e., hand-washable, machine washable, etc.), to be sweat-proof, to sustain stretching of the integrated fabric, to be scalable (e.g., in terms of size, in terms of volume of manufacture, etc.), to be low-maintenance, and to function properly and in a robust manner in relation to seams of the garment. Furthermore, the system 100 is preferably configured to be incorporated into a garment independent of the nature of the particular garment (e.g., underwear, outerwear, loose-fitting, tight-fitting, synthetic material, natural material, or any other characteristics particular to various suitable garments). The system 100 comprises: a fabric interlayer 110 of the garment including a set of ports 115, to which biometric signals can be conducted; an electronics substrate 120 including a set of vias 122; a mount configured to receive and electrically interface a mating object 30 to the electronics substrate 120; and a set of fasteners 150 to mechanically and electrically link the set of ports 115 and the set of vias 122, thereby enabling signal transfer and/or information transfer from the fabric interlayer 110 to a mated object for processing, storage and/or transmission. In one embodiment, the system 100 remaps the pattern of ports 115 from one suitable for manufacture in the fabric interlayer no to one suitable for interfacing with the mating object 30 (e.g., a portable data acquisition and processing unit). The system 100 can additionally or alternatively act as a hub for signals and information routed to the fabric interlayer no from throughout the garment without requiring connections between the disparate regions of the garment where the signals originate and individual data collection/processing modules. As such, the system 100 can provide an improved design for routing signals and biometric information from regions of a garment with integrated sensors while a user is performing a physical activity.

The system 100 is preferably configured to be used by a user who is away from a research or clinical setting, such that the user is interfacing with a portion of the system 100 while he or she undergoes periods of physical activity in a natural, non-clinical setting (e.g., at a gym, outdoors, etc.). The system 100 can additionally or alternatively be configured to be operated by a user who is in a research setting, a clinical setting, or any other suitable setting for the collection of biometric data. Embodiments, variations, and/or examples of the system 100 can be manufactured according to embodiments, variations, and/or examples of the method 200 described in Section 2 below; however, the system 100 can additionally or alternatively be fabricated using any other suitable method.

1.1 System—Supporting Elements

As noted above and as shown in FIG. 12, the system 100 can be integrated with a wearable garment 400. The system 100 is preferably further configured to be in communication with a set of biosensing contacts 500 and a portable control module 30 that couples to the garment 400, in operation, by way of the system 100. The system 100 is preferably affixed to the garment 400 (e.g., using a set of screws, rivets, pins, adhesives, sewing, etc.); However, the system 100 can additionally or alternatively provide coupling between electronic components and/or to the garment 400 by way of one or more of: crimp connectors, snap connectors, stitching, a chemical bond, and any other suitable coupling agent.

The garment 400 is preferably composed of a form-fitting and washable material that is configured to be worn on at least a portion of a user's body. In one variation, the system 100 can be coupled to the exterior of the garment 400, to an inner lining of the garment 400, be removably coupled with respect to any suitable portion of the garment 400, or traverse a portion of the garment. Coupling between the system 100 and the garment 400 can be permanent (e.g., by way of heat binding, by way of gluing, by way of stitching, etc.) or non-permanent (e.g., by using Velcro™, by using fasteners, by using buttons, by using a light adhesive, etc.). The garment 400 can thus include a stretchable and/or compressive fabric comprising natural and/or synthetic fibers (e.g., nylon, lycra, polyester, spandex, etc.) to promote coupling (i.e., electrical coupling, mechanical coupling) and/or reduce motion artifacts that could otherwise result from relative motion between the skin of the user and the system 100.

In examples, the garment 400 can include any one or more of: a top (e.g., shirt, jacket, tank top, bra etc.), bottom (e.g., shorts, pants, capris etc.), elbow pad, knee pad, arm sleeve, leg sleeve, socks, undergarment, neck wrap, glove, and any other suitable wearable garment. Furthermore, the garment 400 can include one or more slots, pouches, ports, bases, pathways, channels, cradles, or other features by which the system 100 and/or set of biosensing contacts 500 can permanently or removably couple to the garment 400.

The set of biosensing contacts 500 function to receive signals from the body of the user, and to transmit signals through the system 100 to the mating object 30 during use by the user. The set of biosensing contacts 500 is preferably an embodiment, variation, or example of the set of biosensing contacts described in U.S. application Ser. No. 14/699,730 entitled "Biometric Electrode System and Method of Manufacture" and filed on 29 Apr. 2015, which is herein incorporated in its entirety by this reference; however, the set of biosensing contacts 500 can additionally or alternatively include any other suitable contacts configured to receive and transmit signals to the system 100.

In relation to the set of biosensing contacts 500, the garment 400 can be configured to position the set of biosensing contacts 500 proximal to one or more of: the pectoralis muscles, the abdominal muscles, the oblique muscles, the trapezius muscles, the rhomboid muscles, the teres major muscles, the latissimus dorsi muscles, the deltoid muscles, the biceps muscles, and the triceps muscles when the garment 400 is worn by the user. Additionally or alternatively, the garment 400 can be configured to position the set of biosensing contacts 500 proximal to one or more of: the gluteus maximus muscles, the gluteus medius muscles, the vastus lateralis muscles, the gracilis muscles, the semimembranosus muscles, the semitendinosis muscles, the biceps femoris, the quadriceps muscles, the soleus muscles, the gastrocnemius muscles, the rectus femoris muscles, the sartorius muscles, the peroneus longus muscles, and the adductor longus muscles when the garment 400 is worn by the user. Variations of the garment 400 can, however, be configured to position the set of biosensing contacts 500 on the body of the user in any other suitable manner or location.

Figure 11:
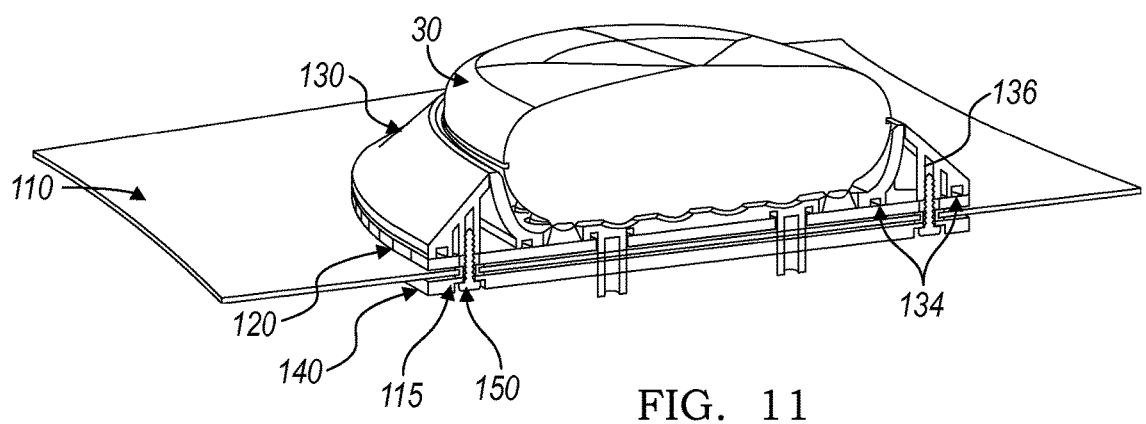
FIG. 11 depicts a cutaway of an example embodiment of the system 100.
Figure 12:
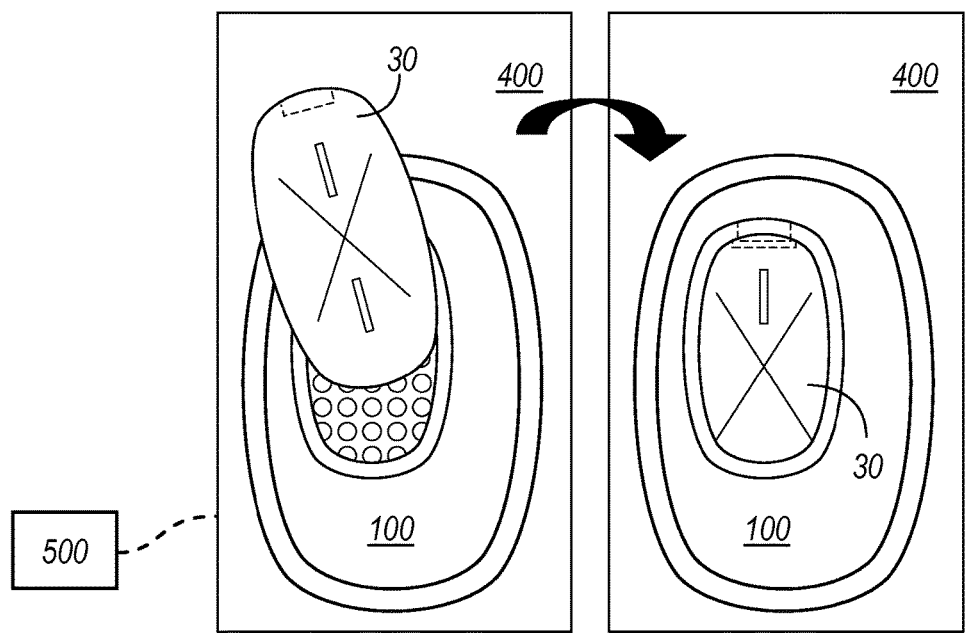
FIG. 12 illustrates the operation of an example embodiment of the system 100 with a mating object 30.

As discussed above, the garment 400 can be configured to couple to and/or communicate with one or more mating objects 30 by means of the system 100. As such, the combination of the garment 400 and the system 100 can provide one or more sites of coupling with the mating object(s) 30 in a manner that does not interfere with activity of the user (e.g., during exercise), while allowing the mating object(s) 30 to interface with all sensor sites governed by the set of biosensing contacts 500. In variations, the mating object(s) 30 can include circuitry for processing signals, storing data, and/or transmitting data, derived from signals received at the set of biosensing contacts 500 and transmitted through the system 100, to a computing device external to the garment 400. Additionally, the mating object 30 preferably cooperates with the system 100 by which the mating object 30 physically couples to the wearable garment 400 and/or by which the mating object 30 electrically couples to the biosensing contacts 500. For example, the mating object 30 can permanently or removably couple to the garment 400 when forming an electrical connection with the system 100, examples of which are shown in FIGS. 11-12. Thus, coupling the mating object 30 to the garment 400 can include depositing the mating object 30 into the system 100 coupled to the garment 400 and in communication with a set of conductive leads of the biosensing contacts 500. In one example embodiment, the system 100 includes both physical coupling elements and electrical coupling elements that establish an electrical coupling between the biosensing contacts 500 and the mating object 30 when the user physically couples the mating object 30 to the system 100. The mating object 30 can include embodiments, variations, and examples of the control module described in U.S. application Ser. No. 14/541,446, entitled "System and Method for Monitoring Biometric Signals" and filed on 14 Nov. 2014; however, the mating object 30 can additionally or alternatively include any other suitable mating object 30.

The system 100 described below can, however, cooperate with or otherwise be integrated with any other suitable elements as described in one or more of: U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, U.S.

application Ser. No. 14/079,621, entitled "Wearable Performance Monitoring, Analysis, and Feedback Systems and Methods" and filed on 30 Jan. 2014, U.S. application Ser. No. 14/699,730, entitled "Biometric Electrode System and Method of Manufacture" and filed on 29 Apr. 2015, and U.S. application Ser. No. 14/724,420, entitled "Biometric Signal Conduction System and Method of Manufacture" and filed on 17 Jun. 2015. Additionally or alternatively, the system 100 can additionally or alternatively be configured to interface with any other suitable element(s).

1.2 System—Overview of Integrated Biometric Signal Interface

As noted above and as shown in FIGS. 1-5, an embodiment of the system 100 includes: a fabric interlayer 110 of the garment including a set of ports 115; a backing plate 140, adjacent to a first side of the fabric interlayer 110, including a set of through holes 145 aligned with the set of ports 115; an electronics substrate 120 having a first surface adjacent to a second side of the fabric interlayer 110 and including a set of vias 122 through a thickness of the electronics substrate 120, aligned with the set of through holes and the set of ports 115, and a set of contacts 124 at a second surface opposing the first surface, each contact in the set of contacts 124 electrically connected to a via in the set of vias 122; a mount assembly 130 having a third surface adjacent to the second surface of the electronics substrate 120 and including a set of blind holes 136 aligned with the set of vias 122, the set of ports 115, and the set of through holes, as well as a set of openings that correspond to and receive portions of the set of contacts, and a fourth surface opposing the third surface and defining a cavity 131 configured to receive and electrically interface the mating object 30 to the electronics substrate 120; and a set of fasteners 150 that 1) compress the backing plate 140, the fabric interlayer 110, the electronics substrate 120, and the mount assembly 130 by way of the set of through holes, the set of ports 115, the set of vias 122, and the set of blind holes 136 in supporting a waterproof seal 134, and 2) electrically couple the set of ports 115 to the set of vias 122. Again, as described in more detail below, one or more variations of the system 100 can omit one or more of the above elements, in providing a suitable interface between a garment and a mating object.

In particular, the set of vias 122 can perform one or more of: functioning as a set of electrical contact points to the set of ports 115, routing an electrical signal from one side of the electronics substrate 120 to another side of the electronics substrate 120, and providing a set of holes through which the set of fasteners 150 can pass. Preferably, the above functions are performed simultaneously, but alternatively the above functions may be performed separately or in any suitable combination. Furthermore, in a specific example, each of the set of vias 122 can include a conductive port through one or more layers of the electronics substrate 120, wherein each via includes a contact pad (configured to make contact with at least one of the set of ports 115) with an opening there through. As described in more detail below, the set of vias can, however, be configured in any other suitable manner.

The system 100 is preferably manufacturable in a manner that is at least partially independent of manufacturing of remaining portions of the garment 400. As such, in one example, an entity (e.g., a manufacturing entity, a user) can affix the system 100 to a garment, as long as the garment provides the appropriate array of ports 115 in a layer of the garment. The layer of the garment providing the appropriate array of ports 115 is preferably a fabric layer, but can alternatively be a non-fabric layer or any suitable portion of the garment. The system 100 in this example can comprise two portions that are removably coupled (e.g., clasped, snapped, or clamped) around the fabric layer such that the ports 115 of the fabric layer are integrated, between the two portions, into the system 100. Alternatively, the system 100 can be manufactured directly into the garment such that it is not easily attached/detached by a user. Furthermore, variations of this example of the system 100 can be designed to couple with any type of garment 400 (e.g., shorts, pants, shirts, etc.) by aligning positions of elements of the system 100 relative to a particular garment 400, without the need to change design aspects of the system 100. Furthermore, variations of this example of the system 100 can be designed to couple with any garment material (e.g., cotton, polyester, Spandex, Lycra, Elastane, etc.) without compromising functionality of the system 100. Therefore, the system 100 can provide improved manufacturing scalability and customization with respect to different types of garments 400.

1.2.1 System—Fabric Interlayer

As shown in FIGS. 3-6, the fabric interlayer 110 preferably includes a set of ports 115 in electrical communication with at least one biometric sensor, and functions to route biometric signals originating from various regions of the garment to the set of ports 115. The fabric interlayer no additionally functions to provide a substrate for the routing of electrically conductive traces 113 integrated into the fabric and for arranging the set of ports 115. The fabric interlayer 110 is preferably an information transfer inlay, examples of which are described in U.S. application Ser. No. 14/742,420, entitled "Biometric Signal Conduction System and Method of Manufacture", filed 17 Jun. 2015, which is incorporated in its entirety herein by reference; however, the fabric interlayer no can alternatively be any suitable portion of the garment at which a set of electrical access points (preferably in the form of ports) to various connected biometric sensors is provided.

In more detail, while the fabric interlayer 110 is preferably flexible and elastic, the fabric interlayer 110 can alternatively comprise regions that are rigid or exhibit flexibility elasticity and rigidity (e.g., by using a combination of rigid and flexible materials) or any combination of the three. In variations, the fabric interlayer no can be composed of one or more of: fabric, cloth, and any other material capable of being stitched together and/or stitched into. In examples, the fabric interlayer no can be composed of one or more of: Polyester, Nylon, Polypropylene, wool, Spandex, and any other natural or synthetic material. In one specific example, the fabric interlayer no can comprise a nylon-spandex composite (e.g., a nylon-spandex circular knit containing 68% nylon and 32% spandex), which is lightweight and can stretch in multiple directions even upon coupling of the system 100 to the garment 400.

Figure 4:
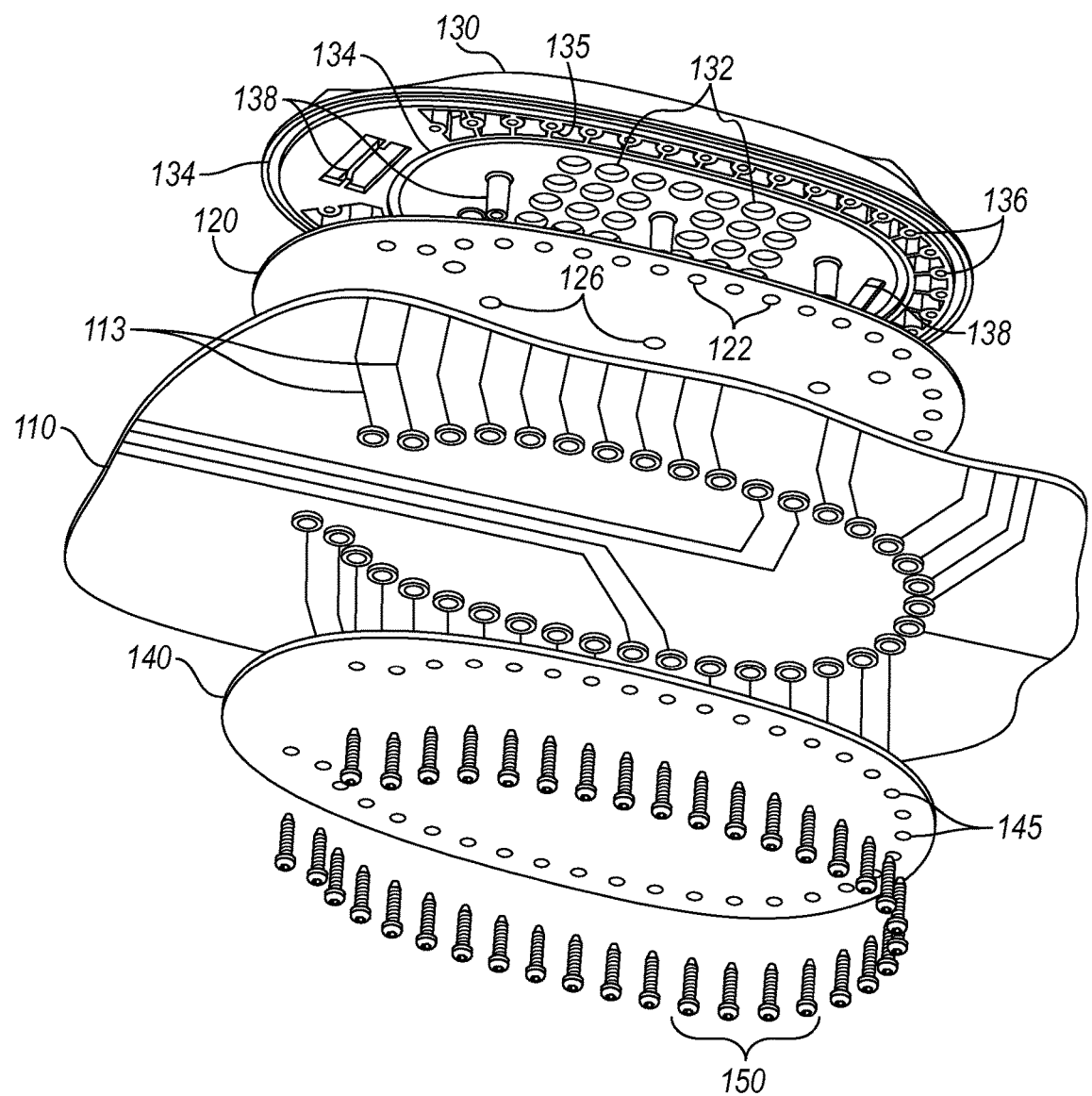
FIG. 4 depicts a second exploded view of an example embodiment of the system 100.
Figure 5:
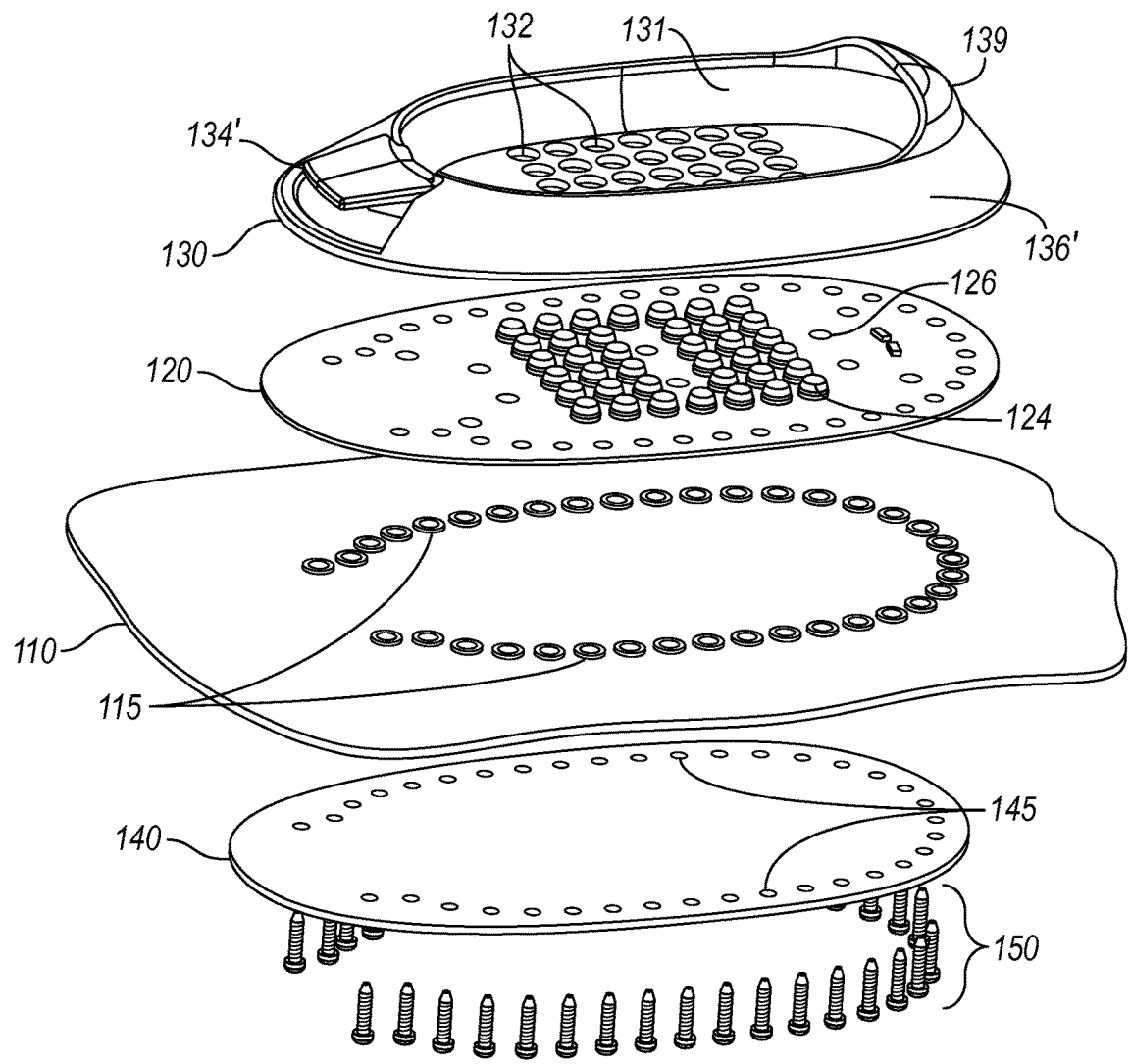
FIG. 5 depicts a third exploded view of an example embodiment of the system 100.
Figure 6:
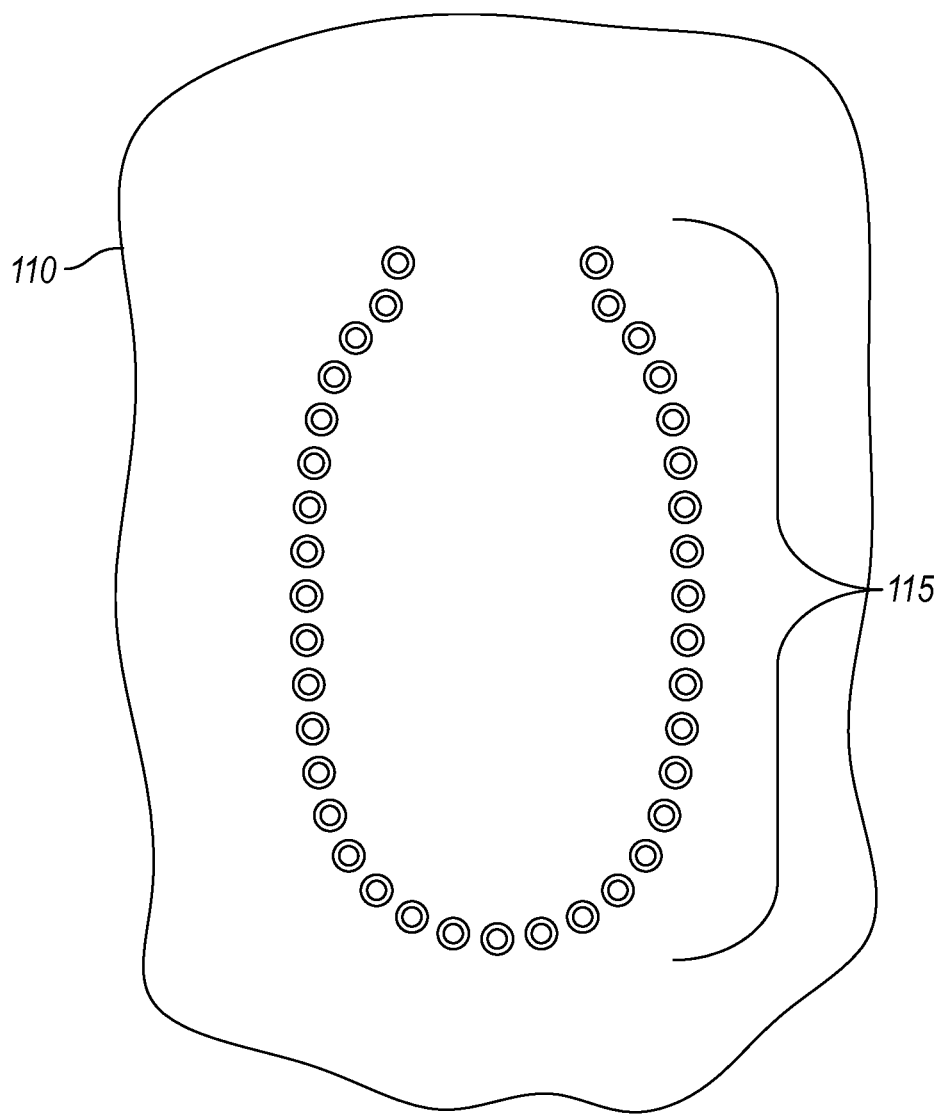
FIG. 6 depicts a schematic of an example embodiment of a portion of the system 100.

As shown in FIG. 4, each port in the fabric interlayer 110 is preferably the terminus of an electrically conductive trace 113 located within a fabric and/or embroidery region of the fabric interlayer no, and preferably provides an electromechanical access point that is electrically coupled to a conductive fabric portion and/or conductive embroidery region of the garment. Preferably, the ports are arranged in the fabric interlayer no as shown in FIGS. 4-6. Alternatively, the port can be located along any portion of the electrically conductive trace 113, or be electrically coupled to the trace 113 in any suitable manner. Preferably, the port is a metallic grommet that is embedded in the fabric interlayer 110 such that at least a portion of the port is accessible from either side of the layer, and that provides a center hole that passes through a thickness of the fabric interlayer no. In an alternative variation, at least one of the ports can be a grommet made of an electrically conductive polymer. However, alternative variations of the port(s) can be composed of any other suitable conductive material.

Furthermore, at least one of the ports can be a raised portion of the fabric interlayer 110, a region of the fabric interlayer 110 that is flush with the surrounding regions of the fabric interlayer no, a solid conductive contact surface, and/or partially or completely covered by an additional conductive layer or layers. In additional alternative variations, the port(s) can comprise any suitable structure that enables electrical communication between the fabric interlayer 110, other portions of the system 100, and at least one biometric sensor coupled to the garment.

1.2.2 System—Electronics Substrate

The electronics substrate 120 is coupled to a first side of the fabric interlayer no, and functions to route electrical signals between the fabric interlayer no and the electronics substrate 120. The electronics substrate 120 includes a set of vias 122 through a thickness of the electronics substrate 120 that are aligned with the set of ports 115 of the fabric interlayer no. The electronics substrate 120 can also include a set of contacts 124, at a surface of the electronics substrate 120 opposing the fabric interlayer no, such that each of the contacts is connected to at least one of the vias. The electronics substrate 120 can thus also function to provide signal routing pathways from the set of vias 122 to the set of contacts 124. The electronics substrate 120 is preferably adjacent to the fabric interlayer no, but can alternatively be separated by one or more additional layers of another material (e.g., fabric, polymer sheet, plastic film, etc.) that provide suitable pathways for electrical continuity between portions of the set of vias 122 and portions of the set of contacts 124. The electronics substrate 120 is preferably a substantially flat plate-like structure with a small thickness (e.g., 0.1-2 mm), but can alternatively have a morphology that conforms to the curvature of the surface of a user's body and/or the fabric interlayer no, and/or can be configured with any suitable morphology that enables the set of vias 122 to interface with the set of ports 115. The electronics substrate 120 is preferably a rigid printed circuit board (PCB), but can alternatively be semi-rigid, flexible, be composed of rigid and flexible regions, or have any other suitable structural consistency. The electronics substrate 120 is preferably made of an electrically insulating material, but can alternatively be partially conductive/semi-conductive, partially or completely coated with an insulating layer, or any suitable combination of insulating and/or conductive portions that prevent unwanted electrical communication between vias in the set of vias 122 or ports in the set of ports 115 (e.g., short-circuiting).

The electronics substrate 120 is preferably mechanically and electrically coupled to the fabric layer by the set of fasteners 150 by way of the set of ports 115 and the set of vias 122, but alternatively can be coupled by any suitable means that provides electrical communication between the set of vias 122 and the set of ports 115 and mechanical support between the fabric layer and the electronics substrate 120. Examples of alternative means of coupling the electronics substrate 120 to the fabric layer include: adhesives, thermal bonding, straps, clips, snaps, and any other suitable coupling means. Examples of alternative means of coupling the set of vias 122 to the set of ports 115 include: snaps, conductive adhesives, clips, wires, welding, soldering, sewing together with conductive thread, or any other suitable electrical coupling means.

In some variations, the set of vias 122 can be coupled to the set of ports 115 in a one-to-one manner, as shown in FIGS. 4-5. Alternatively, a single via can be coupled to a plurality of ports, or a single port can be coupled to a plurality of vias, such that the set of vias 122 and the set of ports 115 are coupled in a non-one-to-one manner. Furthermore, in alternative variations, the system 100 can comprise a single via and/or a single port in the set of vias 122 and the set of ports 115, respectively.

The set of vias 122 preferably comprises a set of vias 122 that pass entirely through the electronics substrate 120 (e.g., a set of through holes with conductive linings). Alternatively, the vias can include one or more blind vias, and/or one or more buried vias. In more detail, each via in the set of vias 122 preferably comprises at least one conductive pad on one or both sides of the electronics substrate. The conductive pad functions as a substantially flat location at which conductive portions of the system 100 can be brought into electrical communication with the via. The pad is preferably at least as large as a projected area of a grommet in variations including a set of grommets, but alternatively can be any suitable size.

The set of contacts 124 can further function to route electrical signals that enter the electronics substrate 120 in a first arrangement defined by the set of vias 122 to a second arrangement defined by the set of contacts 124. Preferably, the first and second arrangements are different, but alternatively they can be similar or identical. Preferably, the second arrangement is more compact than the first arrangement (i.e., the average intra-contact spacing is preferably less than the average intra-via spacing), but alternatively it can be identical or less compact than the first arrangement. Preferably, the second arrangement corresponds to an arrangement of receiving positions on the mating object 30, but can alternatively correspond to any suitable arrangement. The first arrangement can be constrained by, for example: manufacturing processes, material properties, structural characteristics, any other relevant constraint, or any of these constraints applied to the set of ports 115 of the fabric interlayer 110 (with which set of vias 122 are preferably aligned). As such, in examples, the first arrangement can be constrained in terms of one or more of: pattern density, inter-port spacing, a material-related parameter, manufacturability of the fabric interlayer or other portions of the system 100, and any other suitable constraining factor. The second arrangement may not have any constraints, can be optimized to provide a compact interface to the mating object 30, or can be arranged in any other suitable manner. In one example variation, as shown in FIG. 5, the set of ports 115 of the fabric interlayer 110 and the set of vias 122 of the electronics substrate 120 are constrained by a minimum inter-port distance between ports in the fabric interlayer 110 determined by a requirement to avoid short-circuits between ports, and the set of contacts 124 is specifically arranged to interface with a small and/or compact mating object 30 (e.g., a portable control module), such that the constraint associated with the set of ports 115 of the fabric interlayer 110 is different than the constraint associated with the set of vias 122 of the electronics substrate 120. In another related example, the first arrangement of the set of ports 115 of the fabric interlayer 110 follows an open elliptic curve and the second arrangement associated with the set of contacts 124 of the electronics substrate 120 is a rectilinear gridded arrangement.

The set of contacts 124 preferably protrude from a surface of the electronics substrate 120 opposing the surface of the electronics substrate 120 that is coupled to the fabric interlayer 110. In one example, the set of contacts 124 comprises a set of frustoconical protrusions arrayed on the electronics substrate 120. Alternatively, the contacts can be raised from a different surface or not raised at all. The set of contacts 124 preferably is electrically connected to and has a one-to-one correspondence with the set of vias 122. Alternatively, multiple vias can correspond to a single contact, and/or multiple contacts can correspond to a single via. The set of contacts 124 can be electrically connected to the set of vias 122 by a set of electrically conductive traces on and/or in the electronics substrate 120, or any other suitable means of electrical connection (e.g., wiring, soldering, brazing, welding, fastening, etc.) Preferably, the set of contacts 124 comprises contacts composed of an electrically conductive, elastic, and compliant material (e.g., electrically conductive silicone, electrically conductive polymer, etc.) that facilitates maintenance of electrical communication between the contacts 124 and the mating object 30 during motion of the user. Alternatively or additionally, the contacts 124 can be individually spring-loaded in order to maintain electrical communication between the contacts 124 and the mating object 30 when the mating object 30 is coupled to the cavity 131. In one example, the conductive polymer used in the set of contacts 124 comprises a conductive elastomer; However, the set of contacts 124 can alternatively comprise one or more contacts composed of a rigid electrically conductive material (e.g., metal, conductive plastic, etc.) that has been shaped to allow for deflection. For example, the set of contacts 124 can comprise a set of metallic springs.

Figure 8:
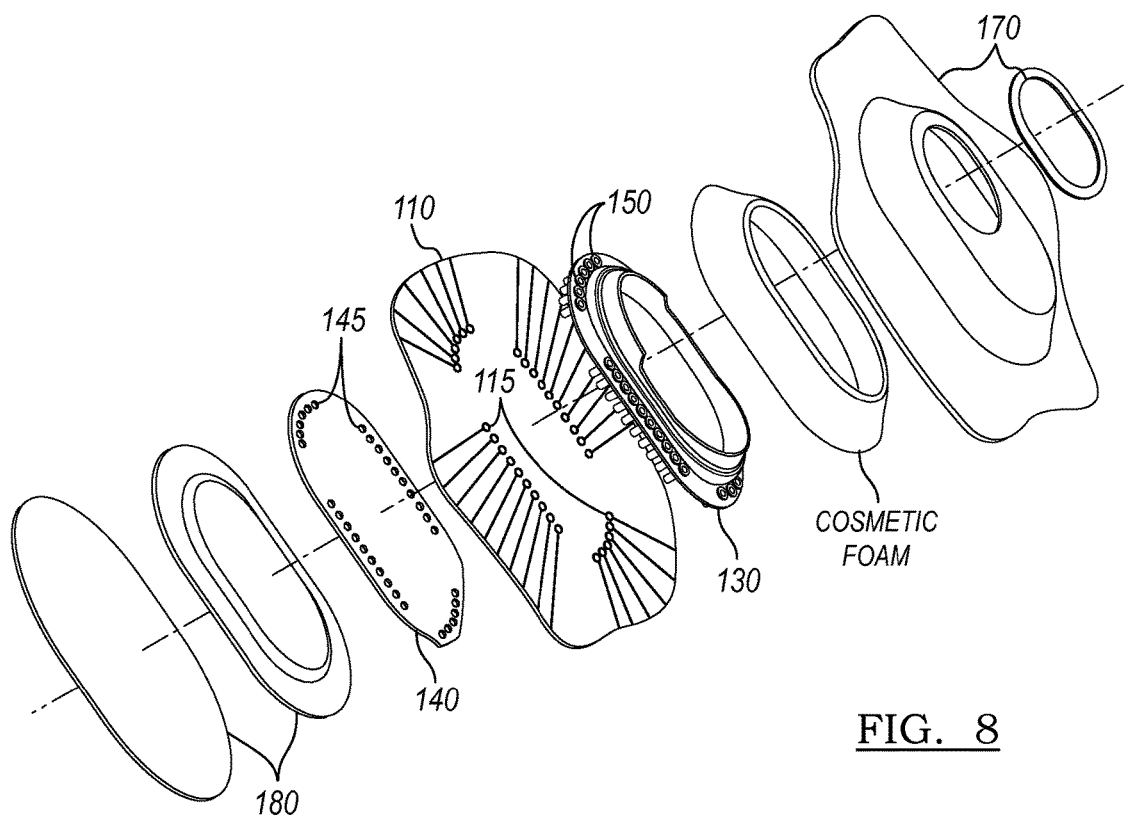
FIG. 8 depicts an exploded view of an alternate example embodiment of the system 100.
Figure 9:
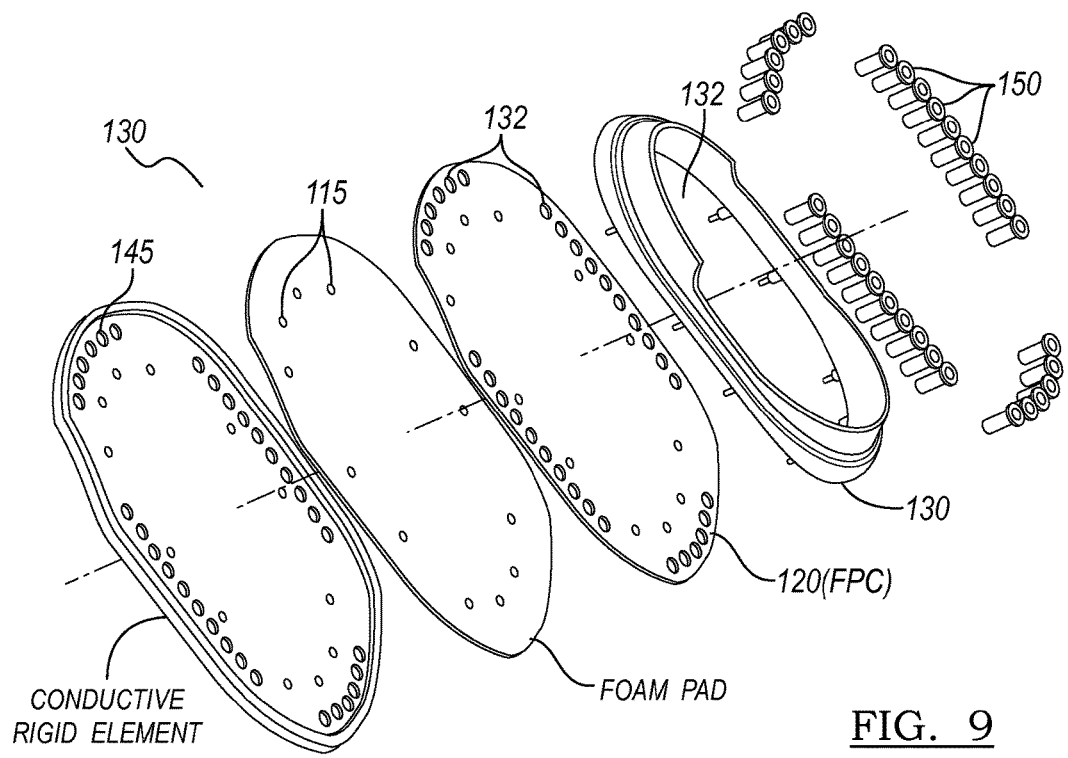
FIG. 9 depicts an exploded view of a portion of an alternate example embodiment of the system 100.

In some variations of the system 100, as shown in FIGS. 8 and 9 (which illustrate exploded views of a portion of the mount interface), the mounting portion can include a flexible circuit board having a plurality of contacts on a top surface of the flexible circuit board. Additionally, the flexible circuit board can include a plurality of vias electrically coupled to corresponding contacts on the flexible circuit board.

The mounting portion, as illustrated in FIGS. 8 and 9, can additionally or alternatively include a compression layer (e.g., foam pad) positioned on a bottom surface of the flexible circuit board. As described above, the compression layer can include foam (e.g., poron foam) or other material capable of compressing when pressure is applied to a top and bottom surface of the compression layer. The compression layer thus functions to support reliable mechanical and electrical contact between the contacts on the surface of the control module and corresponding contact areas on the flexible circuit board of the mount portion.

Alternatively or additionally, the electronics substrate 120 can include one or more through holes 126, blind holes 126, tabs 126, and/or orifices 126 which can function to enable mechanical coupling to other portions of the system 100. For example, one or more through holes in the electronics substrate 120 can receive registration protrusions 138 (e.g., pins, bumps, dowels, etc.) connected to the mount assembly 130. In another example, an edge of the electronics substrate 120 can comprise a series of tabs, configured to receive and mate with a corresponding series of tabs on the mount assembly 130.

In a specific configuration of the electronics substrate 120, a set of traces along the surface of the electronics substrate 120 electrically links the set of vias 122, which are arrayed proximal to the circumference of the electronics substrate 120, to the set of contacts 124, which are raised from the surface of the electronics substrate 120 and arrayed in a rectilinear grid circumscribed by the set of vias 122. This specific example configuration functions to route the electrical signals from the set of vias 122, spaced out from one another according to the spacing of the ports of the fabric interlayer 110, to the set of contacts 124 which are spaced from one another according to the spacing of a set of receiving contacts on the mating object 30, which take the form of a rectilinear grid.

1.2.3 System—Mount Assembly

The mount assembly 130 is preferably coupled to the electronics substrate 120 such that the electronics substrate 120 is disposed between the mount assembly 130 and the fabric interlayer 110, and defines a cavity 131 configured to receive the mating object 30 and electrically interface the mating object 30 with the electronics substrate 120. However, the mount assembly 130 can additionally or alternatively be configured such that the electronics substrate 120 is arranged relative to the fabric interlayer 110 and/or the mount assembly 130 in any other suitable manner. As such, the mount assembly 130 functions to removably couple to and retain the mating object 30 as well as to provide an electrical interface between the mating object 30 and the electronics substrate 120. The mount assembly 130 is preferably made from a molded thermoplastic, but alternatively can be made from a flexible polymer, metal, or any other suitable material via an appropriate manufacturing process.

The mount assembly 130 preferably includes a set of openings 132 within the cavity 131 that are arranged to correspond to the set of contacts 124 of the electronics substrate 120, such that the contacts protrude through the mount assembly 130 and are accessible to the mating object 30 received by the cavity 131. An example instance of the set of openings 132 is shown in FIG. 5. In variations, the mount assembly 130 can include one opening for each contact, can alternatively include openings that do not correspond to a contact, or can alternatively include openings that permit multiple corresponding contacts to pass through the mount assembly 130. The openings are preferably circular, but can alternatively be any suitable shape (e.g., a non-circular shape that corresponds to a non-circular contact shape). Alternatively, there can be one large opening in the mount assembly 130 that does not specifically correspond to the set of contacts 124, as shown in the example depicted in FIG. 1.

Alternatively or additionally, the mount assembly 130 can also include a bevel 136' around an edge of the cavity 131. This preferably provides rigidity to maintain the shape of 131 and ensure that the mating object 30 remains in electrical communication with the system 100 under suitable conditions. This rigidity could also be achieved by removing 136 leaving only a thin wall around 131 and changing the material of 130 to something stiffer (such as metal or fiber reinforced polymers), or any suitable means.

Alternatively or additionally, the mount assembly 130 can also include a partial bezel 139, to assist in retaining the mating object 30. In a variation, an example of which is shown in FIG. 5, the bevel 136' preferably defines the cavity 131, and the partial bezel 139 is positioned at one end of the cavity 131 in order to passively retain one end of the mating object 30 during operation. The partial bezel 139 is preferably convex relative to the base of the cavity 131 as depicted in FIG. 5, but can alternatively be concave relative to the base of the cavity 131, parallel relative to the base of the cavity 131, or any other suitable orientation relative to the base of the cavity 131. The bezel could also be replaced by any geometry, feature or part oriented to suitably retain one end of the mating object 30 during operation.

Alternatively or additionally, the mount assembly 130 can include an adjustable latch 134' which functions to secure/unsecure the mating object 30 to/from the receiving cavity 131 of the mount assembly 130, an example of which is shown in FIG. 5. The latch 134' is preferably a quick-release lever (i.e., requiring a single smooth motion to disconnect the mating object 30 from the mount assembly 130), but alternatively can be an actuator of any suitable type (e.g., a keyed latch, a rotary knob, a press-button, a slider switch, or a clip, etc.). There can alternatively be a plurality of latches 134', wherein some and/or all of the latches must be actuated to connect/disconnect the mating object 30 to/from the receiving cavity 131 of the mount assembly 130. As a further alternative, there can be one or more protrusions and/or recessed portions of the walls of the cavity 131 that can function cooperatively with the latch 134' or latches 134' to retain the mating object 30 in the cavity 131.

Alternatively or additionally, the mount assembly 130 can include a flange 135 around the cavity 131 which functions to provide a substrate for mating connections between the mount assembly 130 and other portions of the system 100. The flange 135 is preferably circumferential as depicted in FIG. 3, but can alternatively be only partially circumferential, or there can be no contiguous flange 135 in favor of a number of discontiguous flanges 135 positioned around the edge of the cavity 131 in any suitable configuration. The flange 135 can also be internal to the edge of the cavity 131, as shown in the example depicted in FIG. 4, and be either contiguous or discontiguous as described above.

Alternatively or additionally, the mount assembly 130 can include a set of holes 136 that function to receive the set of fasteners. The holes 136 are preferably blind holes 136 configured to receive a set of screws, as shown in FIG. 4 and FIG. 11, but can alternatively be through-holes, tapped holes, rivet washers, a male/female portion of a snap or clasp, or any suitable form of mating surface. The holes can alternatively be configured to receive a set of bolts, nails, pins, dowels, buttons, snaps, clasps, or any suitable form of fastener. As a further alternative, the system 100 can include any other suitable mechanism of attaching the mount assembly 130 to other portions of the system 100, such as adhesives, clamps, magnetic attraction, or the like, wherein a set of holes is not required.

Alternatively or additionally, the mount assembly 130 can include one or more seal-supporting features 134 at the side of the mount assembly 130 that is disposed against the electronics substrate 120, which function to receive a sealing component and/or otherwise provide a waterproof seal 134 between the mount assembly 130 and the electronics substrate 120. As shown in FIG. 11, the seal-supporting feature 134 is preferably an O-ring groove which is configured to receive an elastomeric O-ring (i.e., the sealing component), but can alternatively be a ridge configured to retain a gasket, an elastomeric region of the side of the mount assembly 130 itself that is configured to provide the waterproof seal 134 upon compression of the mount assembly 130 against the electronics substrate 120, or any other suitable feature that can function as described above. In variations comprising a plurality of seal-supporting features 134, at least one seal-supporting feature 134 is preferably disposed external to the set of openings 132 which correspond to the set of contacts 124 of the electronics substrate 120 and internal to any additional openings in the mount assembly 130, so as to prevent conductive fluid (e.g., sweat, beverages, etc.) from short-circuiting any of the contacts in the set of contacts 124. In variations including the set of holes configured to receive the set of fasteners, at least one seal-supporting feature 134 is preferably disposed external to the set of holes and at least one seal-supporting feature 134 is preferably disposed internal to the set of holes.

Additionally or alternatively, the mount assembly 130 can include a set of protrusions 138 and/or a set of depressions 138 that function to align with and/or receive alignment surfaces 126 of the electronics substrate 120, as shown in FIG. 3.

1.2.4 System—Fasteners

The set of fasteners 150 is coupled to the fabric interlayer no, the electronics substrate 120, and the mount assembly 130 by way of the set of ports 115 of the fabric interlayer no and the set of vias 122 of the electronics substrate 120, and functions to compress the mount assembly 130, the electronics substrate 120, and the fabric interlayer 110 against one another in supporting a waterproof seal 134 between the mount assembly 130 and the electronics substrate 120, as well as between the electronics substrate 120 and the fabric interlayer 110. The set of fasteners 150 can also function to electrically connect the set of ports 115 of the fabric interlayer 110 to the set of vias 122 of the electronics substrate 120. In an example variation, the set of fasteners 150 is electrically conductive and, upon mechanically joining the fabric interlayer no to the electronics substrate 120, each fastener is in electrical contact with the via and the port through which it passes, thus electrically connecting the port and the via. Preferably, the set of fasteners 150 is a set of screws. Alternatively, the set of fasteners can include any one or more of: a rivet, a nail, a pin, a bolt, a dowel, a clip, a tie, a plug, a wire, and any suitable fastener that can provide compression between the mount assembly 130, the electronics substrate 120, the fabric interlayer 110, and/or any other portion of the system 100.

Figure 7A:
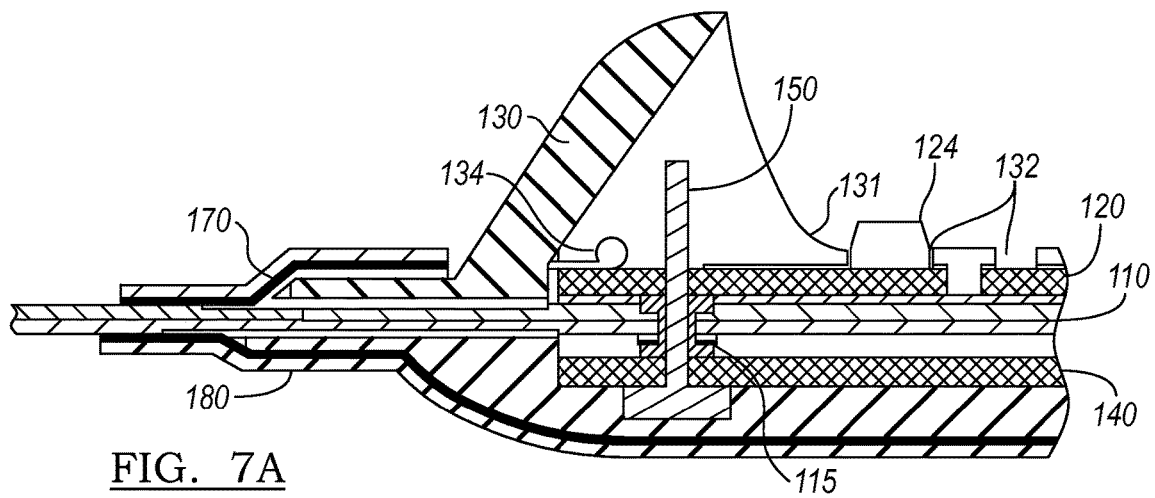
FIGS. 7A, 7B, and 7C depict cross sectional views of various example embodiments of portions of the system 100.
Figure 7B:
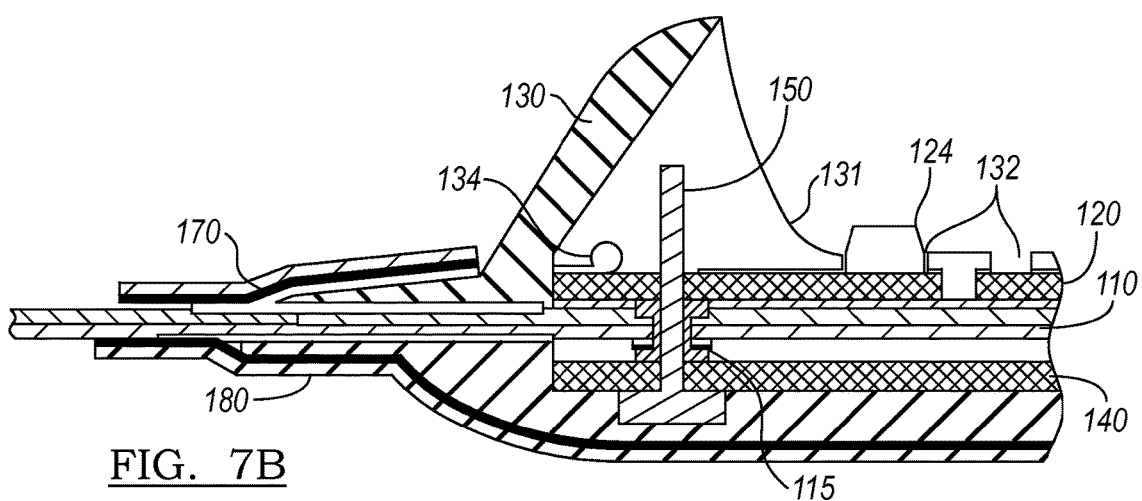
Figure 7C:
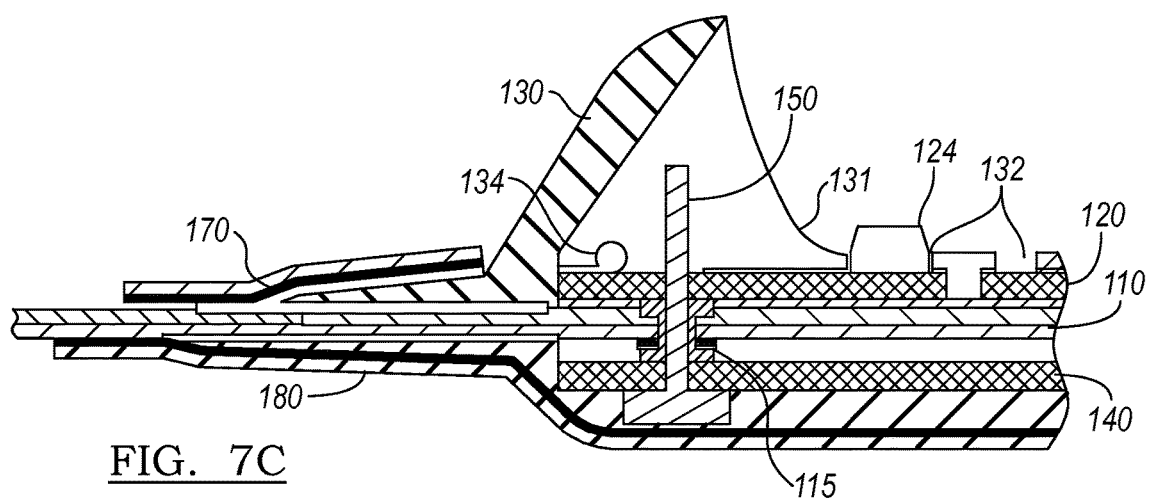

In one variation, depicted in FIGS. 7A,B,C, and 11, the set of fasteners 150 is a set of metal screws wherein each screw passes through a port in the set of ports 115 in the fabric interlayer 110 and a corresponding via in the electronics substrate 120 before being anchored in a blind hole in the mount assembly 130. The set of screws function to compressively hold the fabric interlayer 110, the electronics substrate 120, and the mount assembly 130 together, as well as to electrically connect the set of ports 115 and the set of vias 122. In this variation, the set of ports 115 is preferably a set of metal grommets embedded in the fabric interlayer no, with an internal diameter that is slightly larger than the major diameter of the screws. The set of vias 122 likewise preferably has an internal diameter that is slightly larger than the major diameter of the screw such that the screw. Each screw in the set of screws is preferably screwed into a corresponding blind hole 136 in the mount assembly 130, such as those depicted in FIG. 4, providing a mechanical means against which to pull the fabric interlayer 110 and the electronics substrate 120 in compressing the fabric interlayer 110, the electronics substrate 120, and the mount assembly 130 together. The screw thereby creates a robust electrical connection by pressing the grommets into the contact pads of the vias without the grommets or the vias being damaged or interfering with insertion of the screw.

Figure 10:
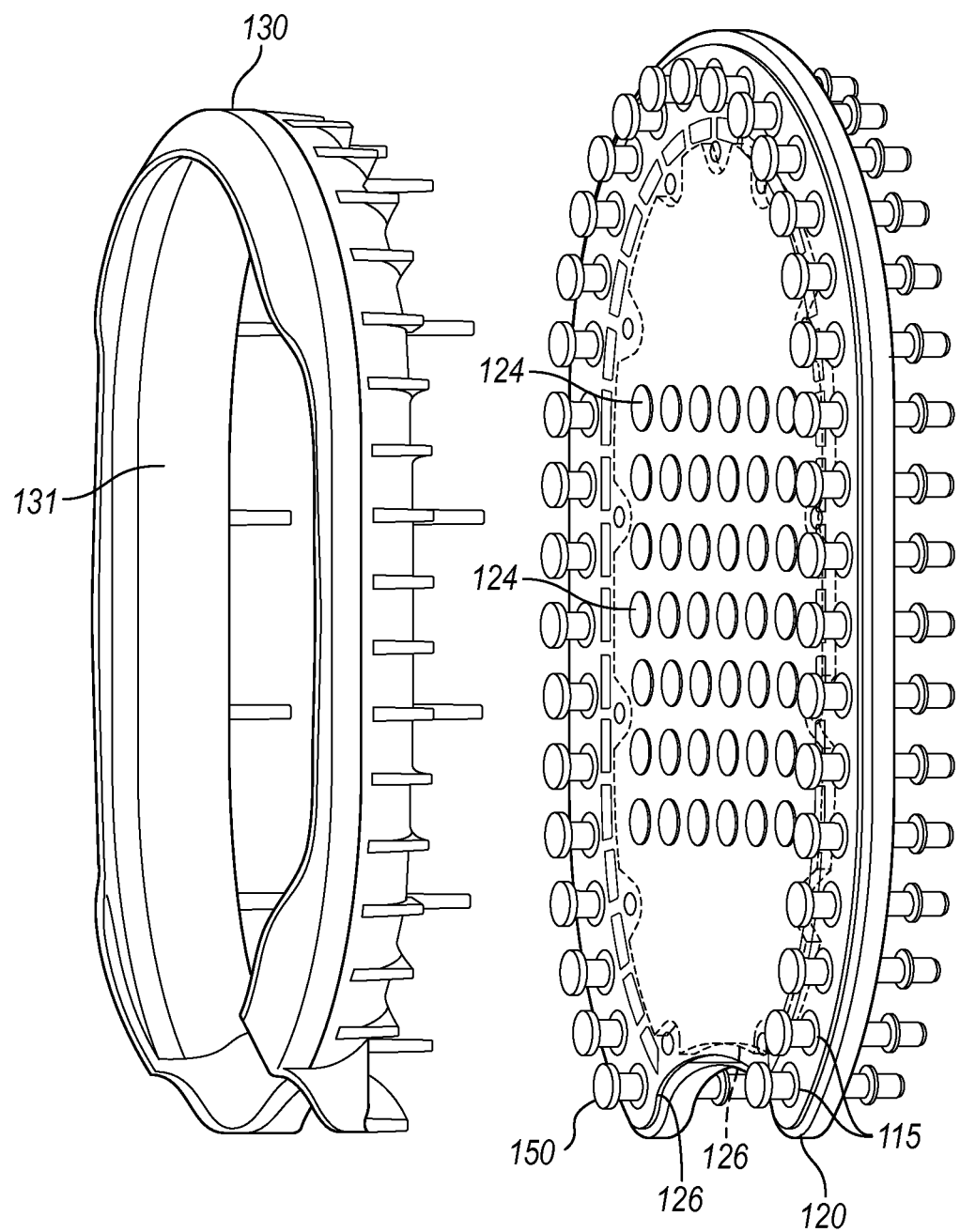
FIG. 10 depicts an illustration of further alternate example embodiments of the system 100.

In another variation, depicted in FIGS. 8-10, the set of fasteners 150 is a set of rivets wherein each rivet passes through a hole in a flange 135 of the mount assembly 130 and a corresponding hole in the fabric interlayer 110. In this configuration, the set of rivets functions to mechanically couple the mount assembly 130 and the fabric interlayer no upon deformation of the tail of the rivet as well as provide the electrical connection from the embroidery on 110 to the traces on 120. In an alternative of this variation, the set of ports 115 of the fabric interlayer 110 comprises a set of rivet washers, and joining the mount assembly 130 to the fabric interlayer 110 via the set of rivets can also function to electrically connect the fabric interlayer 110 to the set of rivets, from which the electrical connections can be routed to the mating object 30.

Additionally or alternatively, the set of fasteners 150 can include a plurality of different types of fasteners, which can function to, according to their type, electrically and/or mechanically couple the fabric interlayer 110 to the electronics substrate 120. For example, the set of fasteners 150 can include a subset of screws and a subset of rivets, wherein the subset of screws functions to mechanically and electrically couple the set of vias 122 of the electronics substrate 120 to the set of ports 115 of the fabric interlayer 110 and the subset of rivets functions only to mechanically couple the electronics substrate 120 to the fabric interlayer no and/or the mount assembly 130. Alternatively, the set of fasteners 150 can include a single type of fastener (e.g., screws) but with only a subset of the set of fasteners 150 providing both mechanical and electrical connections between the electronics substrate 120 and the fabric interlayer no, and the remainder of the set of fasteners 150 providing only mechanical or electrical connections between the electronics substrate 120 and the fabric interlayer no.

1.2.5 System—Backing Plate

The system 100 can optionally include a backing plate 140, coupled to an opposing side of the fabric interlayer 110 from that closest to the electronics substrate 120 and the mount assembly 130, and which includes a set of through holes 145 aligned with the set of ports 115. As such, the backing plate 140 functions to provide a mechanical means against which to compress other portions of the system 100, including the mount assembly 130, the electronics substrate 120, and the fabric interlayer no. The backing plate 140 can function as support for the fabric interlayer no, so as, for example, to prevent deformations (e.g., wrinkling, bunching) of the fabric interlayer 110 that could otherwise interfere with acceptable electrical signal transduction across and/or through the fabric interlayer no.

In variations of the system 100 including a set of fasteners 150 that are configured to pass through portions of the system 100, the set of through holes 145 of the backing plate 140 is preferably configured to receive and correspond to the set of fasteners, such that the backing plate 140 is rigidly coupled to the electronics substrate 120 and the fabric interlayer no is compressed between the backing plate 140 and the electronics substrate 120. Alternatively, the backing plate 140 may not be affixed to the fabric interlayer 110 directly and/or may not compress the fabric interlayer no.

The backing plate 140 is preferably a rigid structure with at least two substantially flat surfaces, of which one is preferably configured to be placed adjacent to the fabric interlayer no such that the backing plate 140 opposes the electronics substrate 120. Alternatively, the backing plate 140 can be flexible or partially flexible, or comprise alternately rigid and flexible regions.

Additionally or alternatively, each through hole in the set of through holes 145 can include a conductive pad situated at a first and/or second side of the backing plate. The conductive pad functions to provide a substantially flat surface at which to bring conductive portions of the system 100 (e.g., the ports of the fabric interlayer) into electrical communication with the backing plate 140 and/or other suitable portions of the system 100 (e.g., a fastener in the set of fasteners 150).

1.2.6 System—External Covers

The system 100 can optionally include one or more external covers, including an inner cover 180 which is coupled to a side of the fabric interlayer 110 that is disposed towards the user and/or wearer of the garment. The inner cover 180 can thus function to protect the fabric interlayer 110 and provide an intermediary layer between the user and portions of the system 100. In variations including a backing plate 140, the inner cover 180 can further function to cover the backing plate 140. The external covers can optionally include an outer cover 170 which is coupled to an opposing side of the fabric interlayer no from the inner cover 180, and which covers at least a portion of the mount assembly 130 while maintaining access to the cavity 131 of the mount assembly 130. The outer cover 170 is preferably bonded to the fabric interlayer no as depicted, for example, in FIGS. 7A,B, and C, wherein the outer cover 170 leaves the cavity 131 region exposed while coupling to the region of the fabric interlayer 110 outside the circumference of the mount assembly 130. In variations including a backing plate 140, the inner cover 180 is preferably bonded to a similar circumferential region of the fabric interlayer no while substantially and/or entirely covering the backing plate 140, as shown, for example, in FIGS. 7A,B, and C.

1.2.7 System—Example Embodiments

In a first example embodiment of the system 100, shown in FIG. 4 and FIG. 5, the system 100 includes a fabric interlayer no, an electronics substrate 120, a mount assembly 130, a backing plate 140, and a set of screws. In this embodiment, the fabric interlayer 110 includes a set of metal grommets which are each coupled to a corresponding conductive thread, each conductive thread embroidered into a portion of the fabric interlayer 110 as shown in FIG. 4. The electronics substrate 120 of this example embodiment includes a set of vias arranged such that each via corresponds to one of the metal grommets, and the center hole of each via is aligned with the center hole of each metal grommet. The electronics substrate 120 also includes a set of protruding, frustoconical contacts arranged in a rectilinear array towards the center of the electronics substrate 120, such that the set of vias 122 is located outside the projected area of the rectilinear array. The electronics substrate 120 also includes a plurality of through-holes that do not correspond to the set of metal grommets. In this embodiment, the mount assembly 130 includes a set of openings 132 arranged such that each opening corresponds to one of the protruding contacts and permits the contact to pass through the thickness of the mount assembly 130. The mount assembly 130 also includes a plurality of protruding posts that are configured to be received by the through-holes in the electronics substrate 120 that do not correspond to the set of metal grommets, such that they can function to cooperatively mechanically couple (e.g., by way of thermally mediated plastic deformation of system components) the mount assembly 130 and the electronics substrate 120. The mount assembly 130 also includes a set of blind holes 136 emplaced in an internal flange 135, such that each blind hole corresponds to a via in the set of vias 122 of the electronics substrate 120. On a side of the mount assembly 130 opposing the set of blind holes 136, the mount assembly 130 includes a bevel 136' around the circumference of the mount assembly 130 such that the bevel 136' defines the cavity 131 that is configured to receive the mating object 30, and the bottom of the cavity 131 includes the set of openings 132. The mount assembly 130 also includes a quick-release latch 134' positioned at one edge of the cavity 131, as well as a partial bezel 139 at an opposing edge of the cavity 131, such that both the latch 134' and the partial bezel 139 are configured to securely retain the mating object 30 and permit efficient de-mating of the mating object 30 when desired by a user. In this embodiment, the backing plate 140 includes a set of through holes 145 that is configured to align with the set of grommets of the fabric interlayer 110 as well as the set of vias 122 of the electronics substrate 120 and the set of blind holes 136 of the mount assembly 130, as shown in FIG. 5. The set of screws is configured to pass through the set of through holes 145 of the backing plate 140 and the set of grommets of the fabric interlayer 110 as shown in FIG. 8, and also through the set of vias 122 of the electronics substrate 120 and into the set of blind holes 136 of the mount assembly 130. In this embodiment, the backing plate 140, the fabric interlayer 110, the electronics substrate 120, and the mount assembly 130 are compressed together by the set of screws, an outer cover 170 is bonded to the fabric interlayer 110 while leaving a portion of the cavity 131 uncovered (as shown by way of example in FIGS. 7A, B, and C), and an inner cover 180 is bonded to the fabric interlayer 110 while covering the entirety of the backing plate 140 (as shown by way of example in FIGS. 7A, B, and C).

In a second example embodiment of the system 100 shown in FIGS. 8-9, the system 100 includes a fabric interlayer 110 with a set of embroidered ports; a backing plate 140, including a first set of through holes 145 with an arrangement corresponding to the set of embroidered ports; a mount assembly 130, including a flange 135 with a second set of through holes 136 with an arrangement corresponding to the set of rivet washers, a bevel 136' defining the edge of the receiving cavity 131, and a fairing that is configured to receive the bevel 136'; a set of rivets, configured to pass through the first and second sets of through holes and the set of embroidered ports; a flexible outer cover 170, including a removable flexible window, and configured to partially enclose the cavity 131 of the mount assembly 130 and receive the removable flexible window so as to fully enclose the cavity 131 of the mount assembly 130 when the flexible window is emplaced; and an inner cover 180, including a spacer layer and an overlayer, such that the spacer layer mates directly to the backing plate 140 and the overlayer covers the entirety of the portion of the system disposed on the inner side of the fabric interlayer no (opposing the mount assembly 130). In this example embodiment, the rivets mechanically and electrically couple to the embroidered ports upon deforming the tails of the rivets, in order to permanently affix the system 100 to the garment via the fabric interlayer 110 and to provide a set of access points to the electrical signals transmitted from regions of the garment to the embroidered ports in the fabric interlayer no.

FIGS. 16-21 depict further example embodiments of portions of the system 100, shown in cross-section. In particular, these FIGURES depict various ways in which portions of the system 100 can be ordered as well as various manners in which electrical signals can be routed through portions of the system 100. These FIGURES are intended solely as examples.

The system 100 can include any other suitable elements configured to enhance electrical and mechanical coupling of a mating object 30 to a garment, to easily and removably couple/decouple the mating object 30 to/from the mount assembly 130, to dissipate static, to shield the conductors from noise, to prevent moisture damage to elements of the system 100, and/or to facilitate manufacturing of the system 100. Furthermore, as a person skilled in the art will recognize from the previous detailed description and from the figures, modifications and changes can be made to the system 100 without departing from the scope of the system 100.

2. Method of Manufacture

Figure 13:
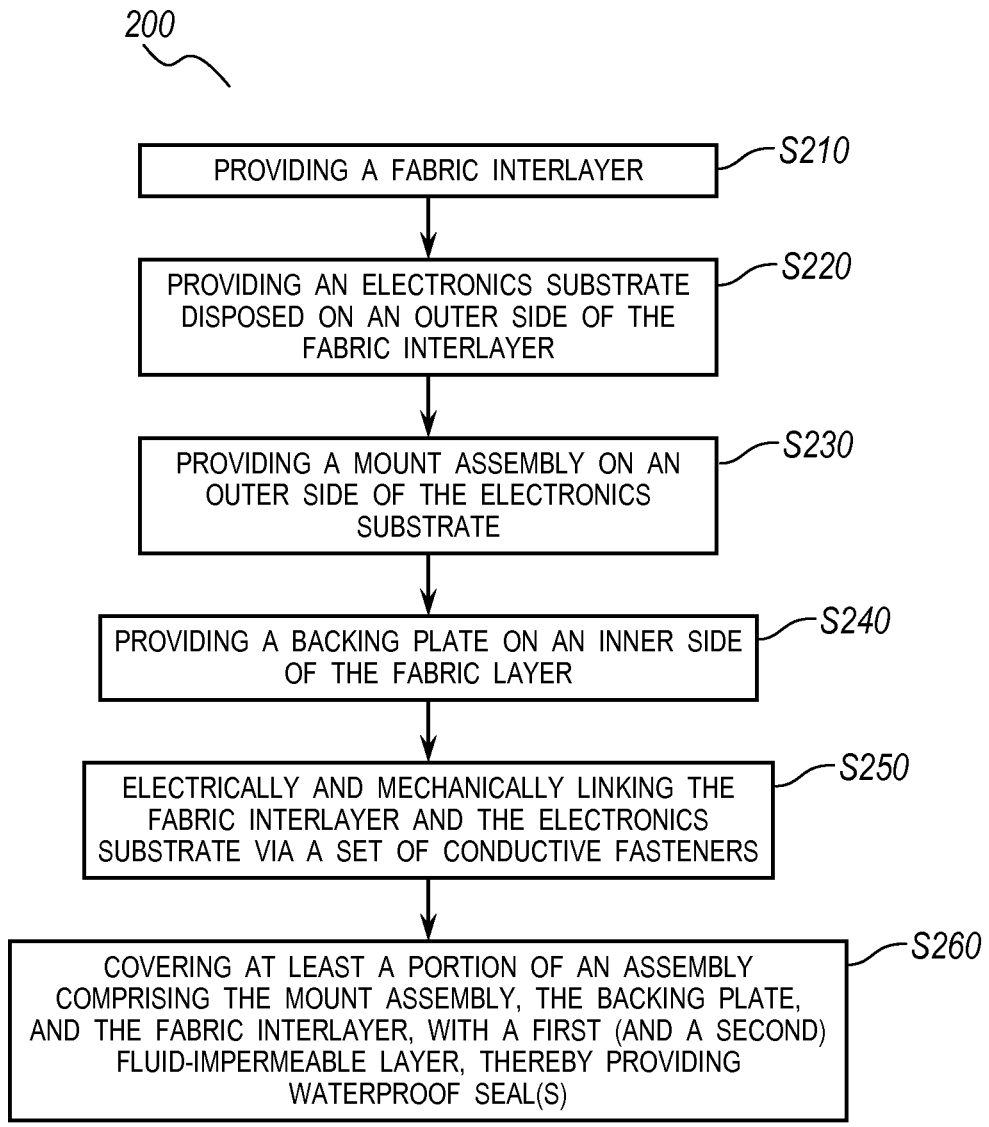
FIG. 13 is a block schematic of a method 200 of manufacture of a system similar to the system 100.
Figure 14:
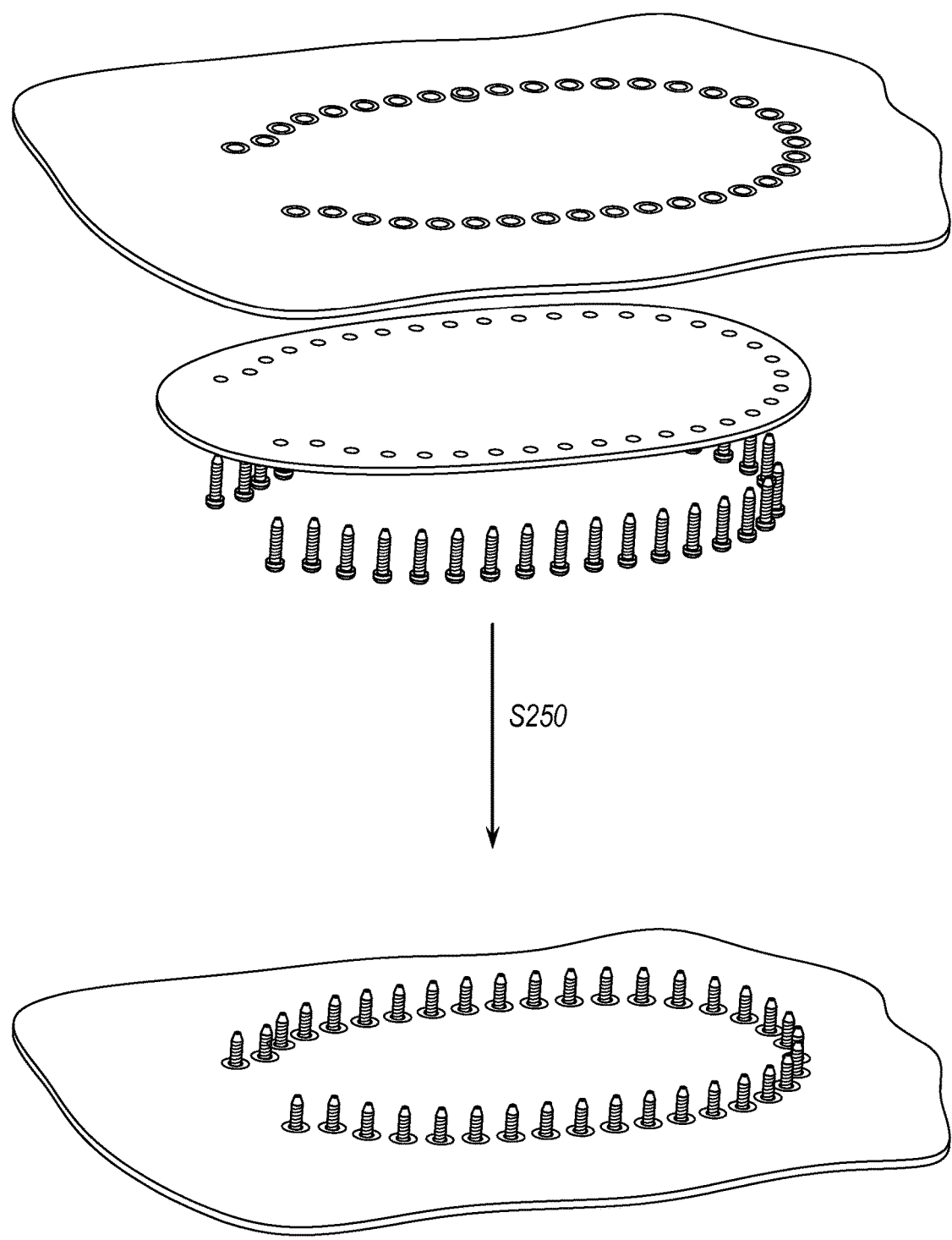
FIG. 14 is a schematic illustration of a portion of Block S250 of the method 200.

As shown in FIG. 13, an embodiment of a method 200 for manufacturing a system for electrically coupling a garment to a mating object comprises: providing a fabric interlayer S210; providing an electronics substrate disposed on an outer side of the fabric interlayer S220; providing a mount assembly on an outer side of the electronics substrate S230; providing a backing plate on an inner side of the fabric layer S240; electrically and mechanically linking the fabric interlayer and the electronics substrate via a set of conductive fasteners S250; covering at least a portion of an assembly comprising the mount assembly, the backing plate, and the fabric interlayer, with a first and a second fluid-impermeable layer, thereby providing waterproof seals S260.

The method 200 functions to produce an electrical interface system that is integrated with a garment intended to be worn by a user while the user performs a physical activity. In particular, the method 200 functions to produce a system that is resistant to damage by fluid associated with an activity performed by an individual, and that retains mechanical and electrical communication with a mating object as the user performs the activity. As such, the method 200 can provide a system configured to facilitate signal transmission associated with one or more of: electromyography (EMG) signals, electrocardiography (ECG) signals, electroencephalograph (EEG) signals, galvanic skin response (GSR) signals, bioelectric impedance (BIA) and any other suitable biopotential signal of the user. The method 200 is preferably configured to produce an embodiment, variation, or example of the system 100 described in Section 1 above; however, in other embodiments, subportions of the method 200 can be adapted to manufacturing portions of any other suitable system.

In providing system elements associated with Blocks S210 through S240, the method 200 preferably includes processing embodiments, variations, and examples of the system elements described in Sections 1.2.1-1.2.3, 1.2.6 above. However, Blocks S210 through S240 can alternatively include provision of any other suitable elements.

Block S250 recites: electrically and mechanically linking the fabric interlayer and the electronics substrate via a set of conductive fasteners. Preferably, the fabric interlayer and the electronics substrate are electrically and mechanically linked with a set of metal screws as described in Section 1.2.4 above, but alternatively they can be linked via any appropriate type of conductive fastener (e.g., rivets, pins, wire, conductive thread, or conductive adhesive).

Figure 15:
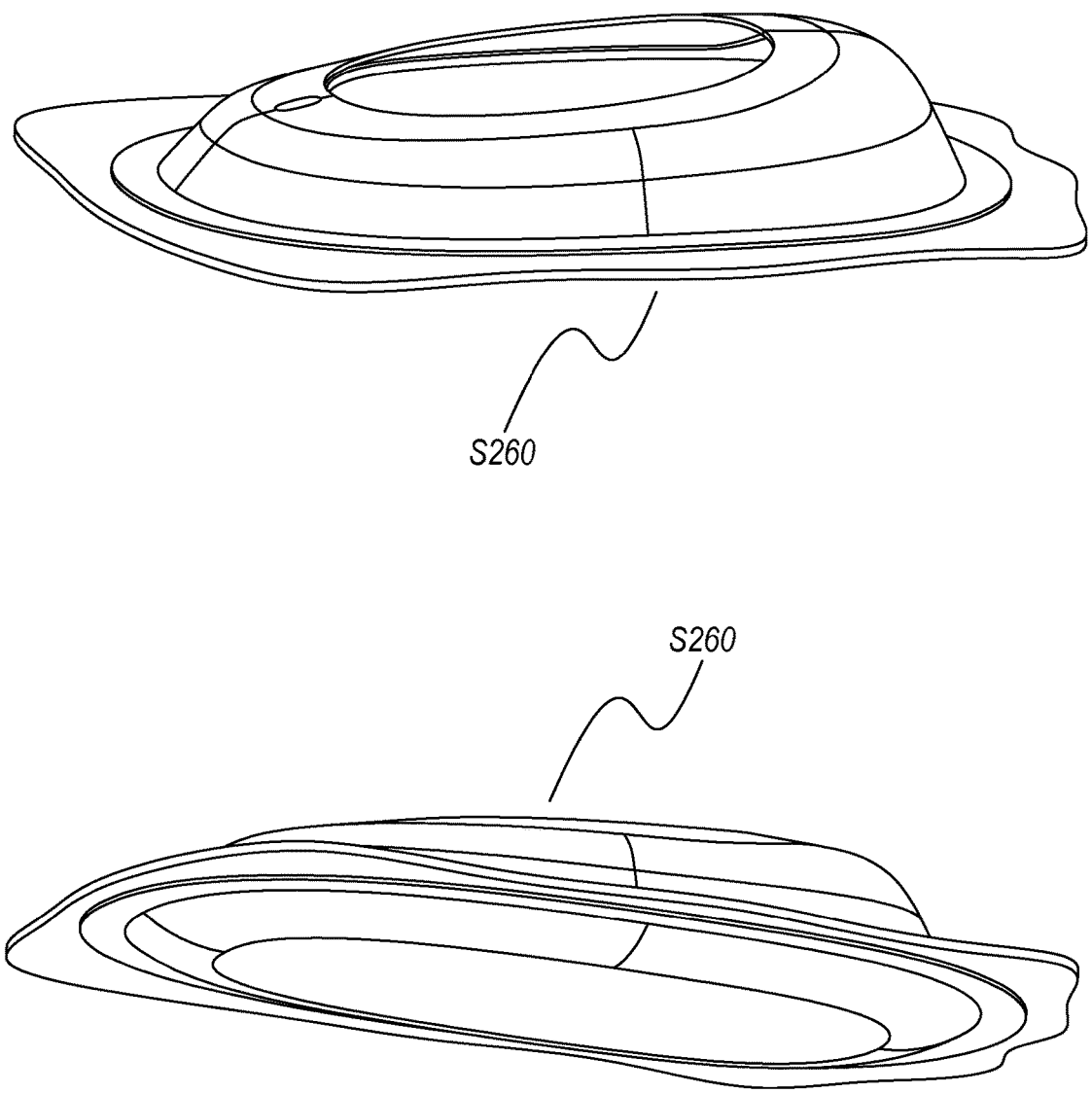
FIG. 15 is a schematic illustration of a portion of Block S260 of the method 200.
Figure 16:
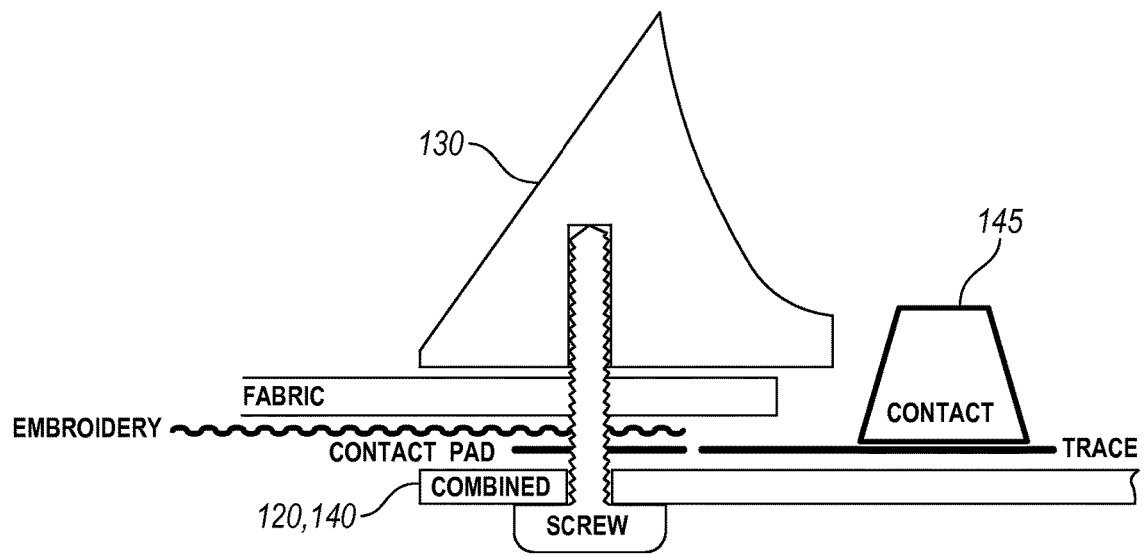
FIG. 16 is a cross sectional view of an example embodiment of the system 100.
Figure 17:
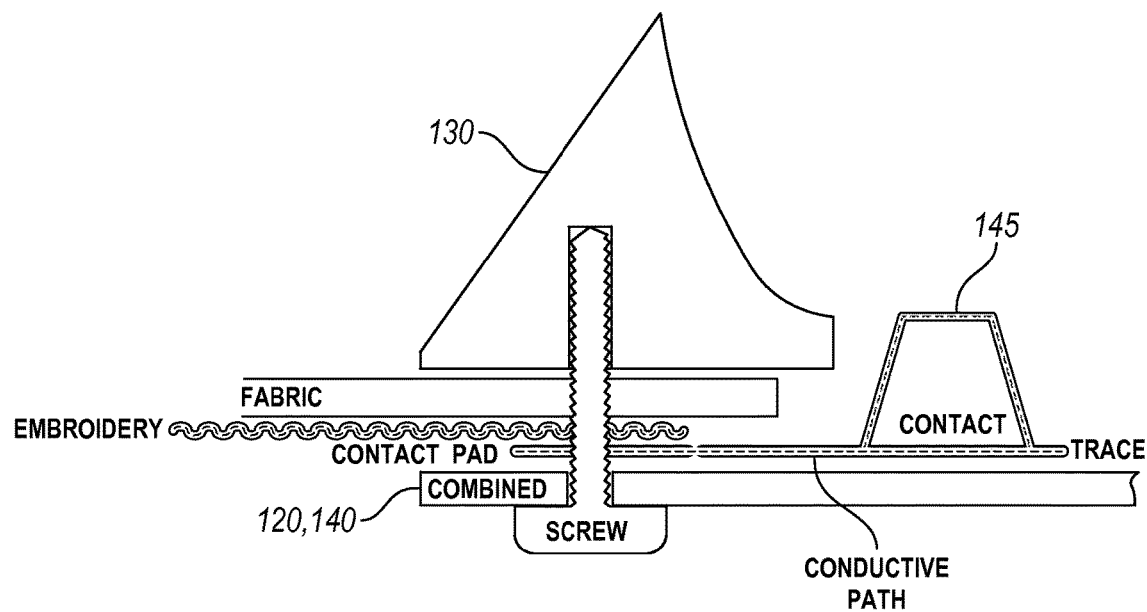
FIG. 17 is a cross sectional view of an example embodiment of the system 100.
Figure 18:
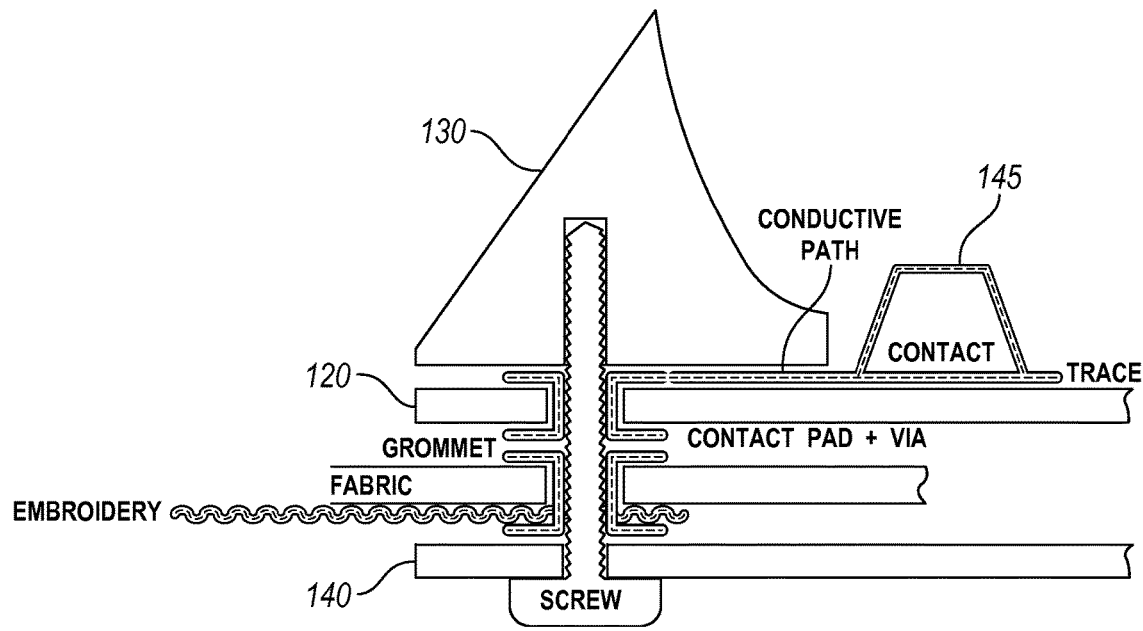
FIG. 18 is a cross sectional view of an example embodiment of the system 100.
Figure 19:
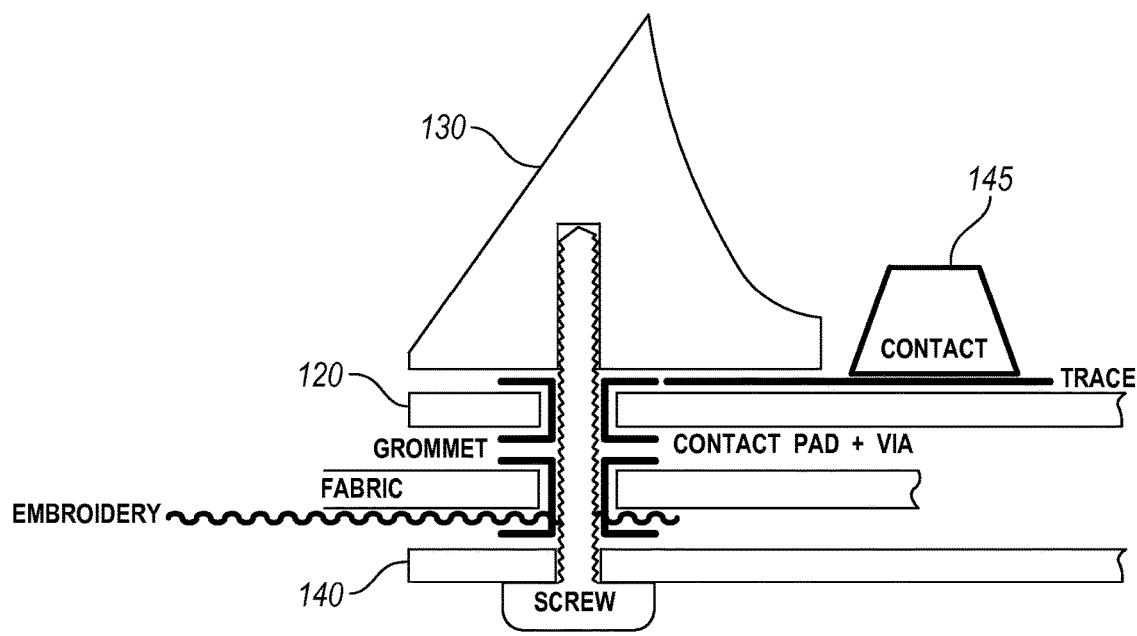
FIG. 19 is a cross sectional view of an example embodiment of the system 100.
Figure 20:
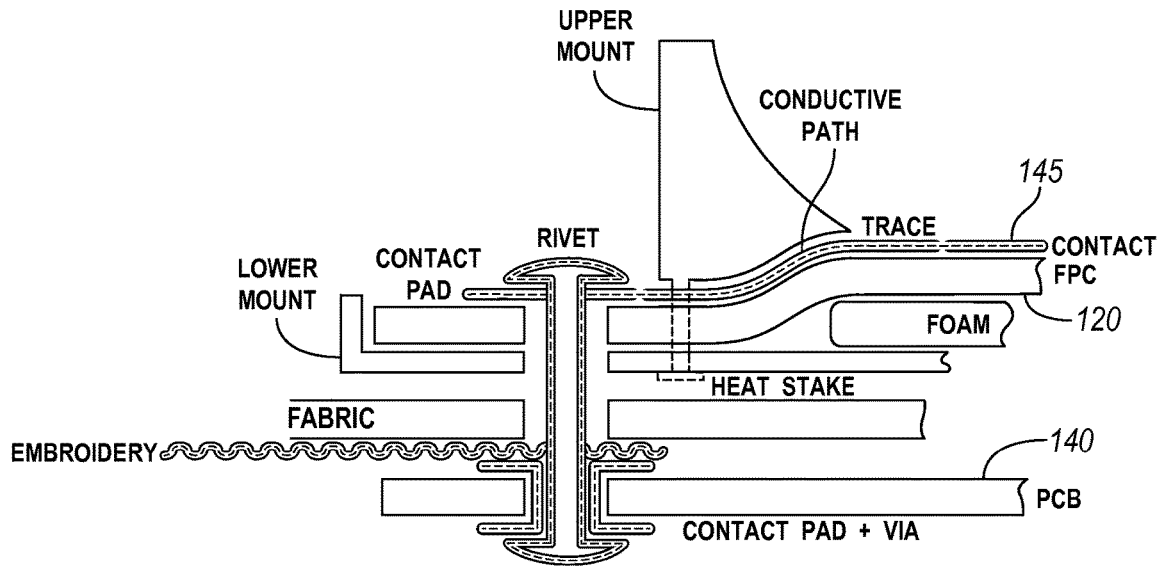
FIG. 20 is a cross sectional view of an example embodiment of the system 100.
Figure 21:
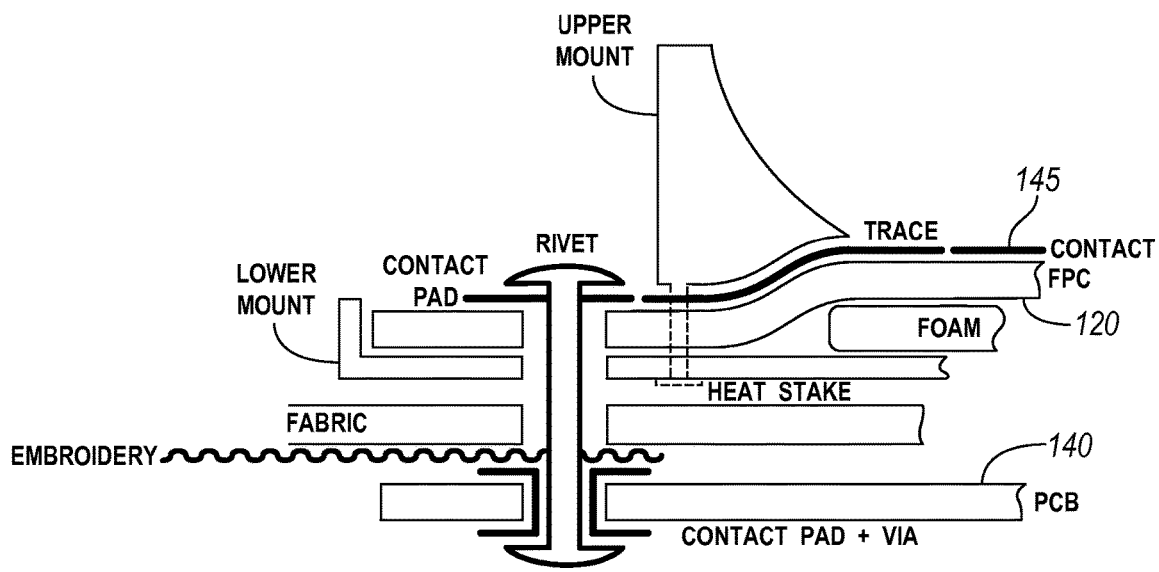
FIG. 21 is a cross sectional view of an example embodiment of the system 100.

Block S260 recites: covering at least a portion of an assembly comprising the mount assembly, the backing plate, and the fabric interlayer, with a first and a second fluid-impermeable layer, thereby completing the multiple layers of waterproof seals. In variations, covering can include bonding a portion of the first and/or second fluid-impermeable layer to a portion of the fabric interlayer, e.g., using a thermal bonding process. Alternatively, covering can include textile-related methods of attachment between the first and/or second fluid-impermeable layer and the fabric interlayer (e.g., sewing, stitching, embroidering, hemming, etc.). Additionally or alternatively, at least one of the first and second fluid-impermeable layers can be omitted and there can be a single layer covering at least a portion of the assembly. An example depiction of the state of the assembly after Block S260 is shown in FIG. 15.

Blocks S210-S260 can include simultaneous implementation of Blocks. Furthermore, Blocks S210-S260 can be performed in any suitable order. For instance, in one such variation, Blocks S260 and S250 can be performed asynchronously, in coupling both fluid-impermeable layers to the fabric interlayer (e.g., using a thermal bonding process after the layers of the system are aligned) prior to securing the electronics substrate to the fabric interlayer via the set of fasteners. Variations of Blocks S210-S260 can, however, be implemented in any other suitable manner.

Embodiments, variations, and examples of the method 200 can thus generate an electronic biosensor mating system that is more fully integrated with a garment, stronger, more water resistant, and requires fewer specialized components, using a process that is less labor-intensive.

Variations of the system 100 and method 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device, and additionally or alternatively, entity performing manual labor, can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams can represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for electrically coupling a garment to a mating object, the system comprising:
   a fabric interlayer of the garment including a set of embedded ports in electrical communication with at least one biometric sensor;
   a backing plate, adjacent to a first side of the fabric interlayer, comprising:
      a set of through holes aligned with the set of embedded ports;
   an electronics substrate having a first surface adjacent to a second side of the fabric interlayer and comprising:
      a set of vias through a thickness of the electronics substrate, and aligned with the set of through holes and the set of embedded ports, and
      a set of raised contacts at a second surface opposing the first surface, each raised contact in the set of raised contacts electrically connected to a via in the set of vias;
   a mount assembly having a third surface adjacent to the second surface of the electronics substrate and comprising:
      a set of blind holes aligned with the set of vias, the set of embedded ports, and the set of through holes,
      a set of openings that correspond to and receive portions of the set of raised contacts, and
      a fourth surface opposing the third surface and defining a cavity configured to receive and electrically interface the mating object to the electronics substrate; and
   a set of fasteners that 1) compress the backing plate, the fabric interlayer, the electronics substrate, and the mount assembly by way of the set of through holes, the set of embedded ports, the set of vias, and the set of blind holes in supporting a waterproof seal, and 2) electrically couple the set of embedded ports and the set of vias,
   wherein at least one embedded port in the set of embedded ports is electrically conductive and secured to the fabric interlayer such that at least a portion of an embedded port is adjacent to the electronics substrate and brought into electrical communication with a via in the set of vias.

2. The system of claim 1 wherein the set of fasteners is a set of electrically conductive screws, and the set of embedded ports is a set of electrically conductive grommets, wherein each electrically conductive grommet comprises a through hole configured to receive an electrically conductive screw in the set of electrically conductive screws.

3. The system of claim 1, further comprising a set of grooves in the third surface, including a first groove and a second groove, wherein the first groove is disposed interior to the set of blind holes and the second groove is disposed exterior to the set of blind holes, and wherein the first groove and the second groove are each configured to receive a corresponding elastomeric ring which, during compression of the mount assembly and the electronics substrate by the set of fasteners, provides a waterproof seal between the mount assembly and the electronics substrate.

4. The system of claim 1, wherein the set of vias are arranged in a first arrangement, and the set of raised contacts are arranged in a second arrangement.

5. The system of claim 4, wherein the first arrangement defines a first average spacing between each via in the set of vias and the second arrangement defines a second average spacing between each raised contact in the set of raised contacts, and the second average spacing is less than the first average spacing.

6. The system of claim 5, wherein the second arrangement corresponds to a set of receiving points on the mating object.

7. A system for electrically coupling a garment to a mating object, the system comprising:
   a fabric interlayer of the garment including a set of embedded ports;
   an electronics substrate adjacent to the fabric interlayer, comprising a set of vias;
   a mount assembly, defining a cavity configured to receive and electrically interface the mating object to the electronics substrate;

a set of fasteners, configured to compress the mount assembly and the electronics substrate against the fabric interlayer in supporting a waterproof seal, each fastener in the set of fasteners concentrically aligned with and passing through an embedded port in the set of embedded ports and a via in the set of vias in providing a mechanical and electrical connection between the embedded port and the via, wherein the set of embedded ports is a set of grommets, wherein at least one grommet in the set of grommets is electrically conductive and secured to the fabric interlayer such that at least a portion of a grommet is adjacent to the electronics substrate and brought into electrical communication with a via in the set of vias.

8. The system of claim 7, further comprising a set of contacts protruding from the electronics substrate, the set of contacts electrically connected to the set of vias and configured to electrically interface the mating object to the electronic substrate by way of the mount assembly.

9. The system of claim 8, wherein the set of contacts has an inter-contact spacing that is less than an inter-via spacing of the set of vias.

10. The system of claim 8, wherein a first arrangement of the set of contacts is constrained by a first constraint, and a second arrangement of the set of vias is constrained by a second constraint.

11. The system of claim 10, wherein the first constraint corresponds to an array of receiving positions on the mating object and the second constraint is a minimum spacing between each conductive trace in a set of conductive traces coupled to the set of embedded ports, and wherein the set of vias is constrained to align with the set of embedded ports.

12. The system of claim 8, wherein each contact in the set of contacts is spring-loaded such that it individually and dynamically resists a force provided by the mating object towards the electronics substrate during operation.

13. The system of claim 8, further comprising a set of grooves in a surface of the mount assembly adjacent to the electronics substrate, wherein a projected area circumscribed by the set of grooves contains an area encompassing the set of openings, and wherein each groove in the set of grooves is configured to receive a corresponding elastomeric ring which, during compression of the mount assembly and the electronics substrate by the set of fasteners, provides a waterproof seal between the mount assembly and the electronics substrate.

14. The system of claim 8, further comprising a set of openings in the mount assembly, the set of openings configured to receive a portion of the set of contacts.

15. The system of claim 7, further comprising a backing plate adjacent to the fabric interlayer such that the fabric interlayer is disposed between the backing plate and the electronics substrate, wherein the backing plate is compressed against the fabric interlayer, the electronics substrate, and the mount assembly by the set of fasteners in supporting the waterproof seal.

16. The system of claim 15, further comprising a first liquid-impermeable layer covering at least a portion of the mount assembly and affixed to the fabric interlayer at a first side, and a second liquid-impermeable layer covering at least a portion of the backing plate and affixed to the fabric interlayer at a second side opposing the first side.

17. The system of claim 7, wherein the set of fasteners is a set of screws, each screw in the set of screws anchored in one of a set of holes in the mount assembly.

18. The system of claim 7, wherein the mount assembly further comprises a latch, coupled to the cavity, configured to removably couple the mating object to the cavity during operation.

19. They system of claim 7, wherein each embedded port in the set of embedded ports comprises a female portion of a metal snap coupler, and wherein each via in the set of vias of the electronics substrate comprises a male portion of the metal snap coupler, and the set of vias is removably coupled to the set of embedded ports by way of mating the female portion and the male portion of each metal snap coupler.

* * * * *